United States Patent [19]

Yoshioka et al.

[11] Patent Number: 5,753,214
[45] Date of Patent: May 19, 1998

[54] BASE MATERIAL FOR COSMETICS AND USES OF THE SAME

[75] Inventors: Masato Yoshioka; Hiroshi Shintani; Takashi Adachi; Emi Segawa, all of Higashiosaka, Japan

[73] Assignee: Seiwa Kasei Co., Ltd., Osaka-fu, Japan

[21] Appl. No.: 512,220

[22] Filed: Aug. 7, 1995

[30] Foreign Application Priority Data

Aug. 24, 1994 [JP] Japan .................................. 6-224132
Aug. 30, 1994 [JP] Japan .................................. 6-230348

[51] Int. Cl.⁶ ................. A61K 7/075; A61K 31/695; A61K 7/11
[52] U.S. Cl. ..................... 424/70.2; 424/70.122; 514/2; 514/12; 514/18; 514/19
[58] Field of Search ................... 424/70.122, 70.2

[56] References Cited

U.S. PATENT DOCUMENTS

| 5,100,956 | 3/1992 | O'Lenick, Jr. .................. 525/54.1 |
| 5,412,074 | 5/1995 | Jones et al. . | |

FOREIGN PATENT DOCUMENTS

| 0 540 357 A2 | 5/1993 | European Pat. Off. . |
| 59-110609 | 6/1984 | Japan . |
| 63-310812 | 12/1988 | Japan . |
| 3-223207 | 10/1991 | Japan . |
| 2 159 408A | 12/1985 | United Kingdom . |

*Primary Examiner*—Peter F. Kulkosky
*Attorney, Agent, or Firm*—Armstrong, Westerman, Hattori, McLeland & Naughton

[57] ABSTRACT

A base materials for cosmetics which comprises a silylated peptide of the formula (I):

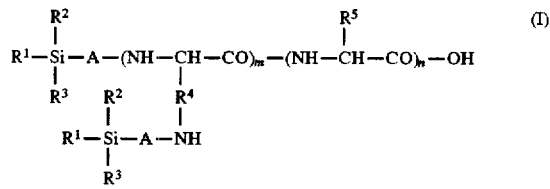

wherein $R^1$, $R^2$ and $R^3$ are the same or different and each is methyl group or hydroxyl group, $R^4$ is a group bonding the terminal amino group in a side chain of a basic amino acid to the α-carbon atom wherein the side chain —$R^4NH_2$ may partly form an N-heterocyclic ring, $R^5$ is a side chain of an amino acid other than the above basic amino acid, A is methylene, propylene, —$CH_2OCH_2CH(OH)CH_2$— or —$(CH_2)_3OCH_2CH(OH)CH_2$— group, m is 0 to 100, n is 0 to 100, and m+n is 1 to 100, provided that m and n only show the number of amino acid units, but not amino acid sequence. The silylated peptide (I) is very useful as an additive for hair and skin cosmetics, particularly for aqueous cosmetics, and have excellent pH and storage stabilities and excellent properties such as gloss and moisture impartment to hairs and skins, improvement of combability of hairs, prevention of hairs from being damaged, restoration of damaged hairs, smoothing skin, and the like.

16 Claims, No Drawings

BASE MATERIAL FOR COSMETICS AND USES OF THE SAME

BACKGROUND OF THE INVENTION

The present invention relates to a silylated peptide useful as a base material for cosmetics and uses thereof. More particularly, the present invention relates to a cosmetics base material comprising a silylated peptide wherein a functional group containing only one silicon atom is bonded to an amino group of a peptide by covalent bond, and which is soluble in water and which, when incorporated into hair cosmetics and skin cosmetics, imparts luster and moisture to hair, improves the combability of the hair, prevents the hair from splitting and imparts luster and moisture to skin to smooth the skin, and moreover, which is so excellent in pH stability and storage stability as to cause no turbidity or precipitation. The present invention also relates to a cosmetic composition containing the cosmetics base material, such as hair treatment, shampoo, first liquid for cold waving solution, hair dye, water-soluble hair dressing or other hair or skin cosmetics.

It has been attempted to incorporate both a silicone oil (organic silicone compound) and a polypeptide to hair cosmetics for the purpose of exhibiting excellent properties of the silicone oil such as extensibility, gloss imparting property to hair and hair protecting action resulting from impartment of water-repelling property to hair, and properties of the polypeptide such as sorption action to hair, relaxation action for skin stimulation, and protective and moisture-keeping actions based on film formation.

For example, Japanese Patent Publication Kokoku No. 63-5005 proposes a hair cosmetic incorporated with a hydrophobic silicone oil and a salt of a lower alkyl ester of a mono-N-long chain acyl basic amino acid. Japanese Patent Publication Kokai No. 63-310812 proposes a hair treatment incorporated with dimethyl polysiloxane or methyl phenyl polysiloxane and a hydrolyzed collagen.

However, silicone oils are hydrophobic (lipophilic) compounds and polypeptides are hydrophilic compounds, so they are poor in compatibility with each other. Accordingly, when they are used in combination, commodity value as cosmetics is apt to be impaired because the emulsion stability is low and separation is easy to occur. Also, the polypeptides are hard to attach to a portion of the hair which has contacted the silicone oils in advance of the polypeptides, and conversely the silicone oils are hard to attach to a portion of hair which has contacted the polypeptides in advance of the silicone oils, so the combination use of the silicone oils and the polypeptides has a problem that the properties of them cannot be sufficiently exhibited.

In order to eliminate these disadvantages in the combination use of silicone oils and polypeptides, it is proposed in Japanese Patent Publication Kokai No. 3-223207 to synthesize a compound having both the properties of silicone oils and the properties of polypeptides by reacting a hydrophobic silicone oil and a hydrophilic polypeptide and to use it as a base material for cosmetics, thereby exhibiting properties that silicone oils and polypeptides possess. However, this peptide-modified silicone derivative is poor in pH stability and storage stability in water owing to influence of the water slightly soluble or water insoluble silicone segment. Since hair cosmetics and skin cosmetics are mainly soluble in water, it causes a problem of occurrence of turbidity or precipitation during storage. Further, since the reaction of the water slightly soluble or water insoluble silicone oil and the water-soluble polypeptide is conducted in water, the reactivity is low and accordingly the yield is low. The production of the peptide-modified silicone derivative has a problem that a water-miscible organic solvent such as an alcohol must be added to the reaction system when an increased yield is desired.

Accordingly, it is an object of the present invention to provide a base material for cosmetics which has both excellent properties of silicone oils and excellent properties of polypeptides and moreover which has excellent pH and storage stabilities in water and accordingly can be stably used in cosmetics without causing turbidity or precipitation during the storage.

Another object of the present invention is to provide cosmetics containing such a base material.

These and other objects of the present invention will become apparent from the description hereinafter.

SUMMARY OF THE INVENTION

It has now been found that a silylated peptide of the formula (I):

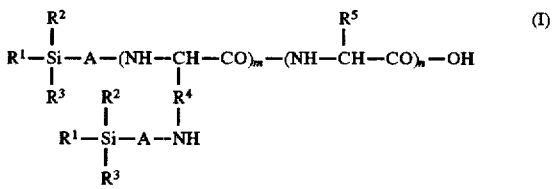

wherein $R^1$, $R^2$ and $R^3$ are the same or different and each is methyl group or hydroxyl group, $R^4$ is a residue of a basic amino acid having an amino group at the end of a side chain wherein the terminal amino group and the group —CH(NH$_2$)COOH are excluded from the basic amino acid, $R^5$ is a side chain of an amino acid other than the above basic amino acid, A is methylene, propylene, —CH$_2$OCH$_2$CH(OH)CH$_2$— or —(CH$_2$)$_3$OCH$_2$CH(OH)CH$_2$— group, m is 0 to 100, n is 0 to 100, and m+n is from 1 to 100, provided that m and n only show the number of amino acid units, but not amino acid sequence, is soluble in water and has excellent pH stability and storage stability in water, and moreover has both excellent properties as derived from silicone oils and excellent properties as derived from polypeptides, and when incorporated into hair cosmetics or skin cosmetics, it imparts gloss and moisture to hair, improves combability of hair, prevents hair from splitting, imparts gloss and moisture to skin and smoothes the skin, in particular, when incorporated into detergents or cleansers such as shampoo, it serves to produce foams having a soft feeling and smoothes the hair or skin after use and moreover it does not cause turbidity or precipitation during the storage.

In accordance with the present invention, there is provided a base material for cosmetics which comprises a silylated peptide of the formula (I):

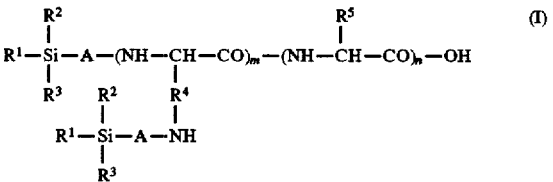

wherein $R^1$, $R^2$ and $R^3$ are the same or different and each is methyl group or hydroxyl group, $R^4$ is a residue of a basic amino acid having an amino group at the end of a side chain wherein the terminal amino group and the group —CH(NH$_2$)COOH are excluded from the basic amino acid, $R^5$ is a side chain of an amino acid other than the above basic amino acid, A is methylene, propylene, —CH$_2$OCH$_2$CH(OH)CH$_2$— or —(CH$_2$)$_3$OCH$_2$CH(OH)CH$_2$— group, m is 0 to 100, n is 0 to 100, and m+n is from 1 to 100, provided that m and n only show the number of amino acid units, but not amino acid sequence.

The silylated peptide (I) is very useful as an additive for hair and skin cosmetics, particularly for aqueous cosmetics, and can be used in various cosmetics.

Accordingly, in another aspect, the present invention provides a cosmetic composition containing a proper amount of the silylated peptide (I).

DETAILED DESCRIPTION

The present invention is explained below in detail from the viewpoints of the structure and properties of the silylated peptide, actions of the silylated peptide onto the hair and skin, peptides and silyl compounds used in the synthesis of the silylated peptide, synthesis of the silylated peptide, uses of the base material for cosmetics comprising the silylated peptide and cosmetics incorporated with the base material.

[Structure and Properties of Silylated Peptide]

The silylated peptides of the present invention are represented by the formula (I):

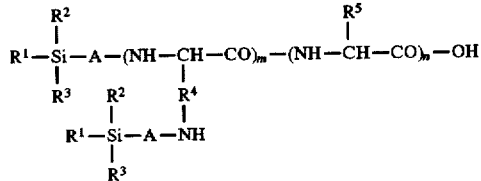  (I)

wherein R$^1$, R$^2$ and R$^3$ are the same or different and each is methyl group or hydroxyl group, R$^4$ is a residue of a basic amino acid having an amino group at the end of a side chain wherein the terminal amino group and the group —CH(NH$_2$)COOH are excluded from the basic amino acid, R$^5$ is a side chain of an amino acid other than the above basic amino acid, A is methylene, propylene, —CH$_2$OCH$_2$CH(OH)CH$_2$—or —(CH$_2$)$_3$OCH$_2$CH(OH)CH$_2$— group, m is 0 to 100, n is 0 to 100, and m+n is from 1 to 100, provided that m and n only show the number of amino acid units, but not amino acid sequence. The silylated peptides (I) are modified peptides wherein at least two functional groups containing only one silicon atom are bonded to amino groups, including an amino group in an amino acid side chain, of a peptide by covalent bond.

The term "amino group" as used in the definition of the formula (I) comprehends NH< group present in a terminal N-heterocyclic group such as imidazolyl group.

The silylated peptides of the present invention are obtained, for instance, by reacting peptides of the formula (II):

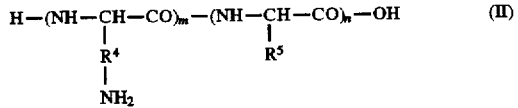  (II)

wherein R$^4$, R$^5$, m and n are as defined above, with silyl compounds of the formula (III):

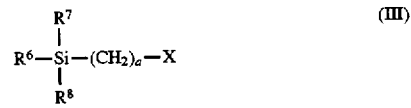  (III)

wherein R$^6$, R$^7$ and R$^8$ are the same or different and each is methyl group, methoxy group, ethoxy group, hydroxyl group or a halogen atom, X is a halogen atom and a is 1 or 3 or silyl compounds of the formula (IV):

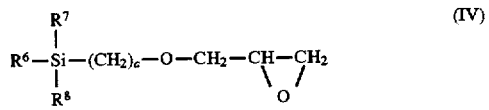  (IV)

wherein R$^6$, R$^7$, R$^8$ and a are as defined above.

Since the silylated peptides represented by the formula (I) have, as apparent from the structural formula therefor, a silyl functional group portion containing a silicon atom derived from the silyl compounds (III) or (IV) and a peptide portion derived from the peptides (II), they can simultaneouly exhibit excellent extensibility, friction-reducing property, gloss-imparting property and water repellency-imparting property which are based on the silyl functional portion, and excellent sorption action, actions of increasing the volume of hair and of imparting elasticity to hair resulting from the sorption, protective action by film formation and hygroscopicity which are based on the peptide portion.

Since the reaction of the hydrophilic peptides and the hydrophobic silyl compounds to produce the silylated peptide (I) is carried out in water, the alkoxyl group, halogen atom or other hydrolyzable groups attaching to the silicon atom are hydrolyzed to wholly or partially change into hydroxyl group, thus the reaction products become soluble in water. Further, since the molecular structure of the silyl functional portion is smaller than the hydrophilic peptide portion, the reaction products have an improved water solubility, thus the silylated peptides of the present invention have an improved storage stability in water as compared with conventional peptide-modified silicone compounds.

Since the silyl compounds (III) or (IV) contain only one silicone atom, the film forming property of the silyl compounds themselves is inferior to high molecular weight silicones (degree of polymerization: 10 to 1000) which have been generally incorporated into cosmetics. However, in the silylated peptides (I), a plurality of the functional groups each containing only one silicon atom (hereinafter referred to as "silyl functional group"), e.g. several silyl functional groups, are introduced to one peptide chain by the reaction with the terminal amino group of a peptide and the amino group or groups in the side chain or chains of an amino acid in the peptide. Therefore, the silylated peptides of the present invention can exhibit similar actions to the polymeric silicones, such as excellent extensibility, friction-reducing property, gloss-imparting property and water repellency-imparting property based on the silyl compounds.

It is preferable that the rate of introduction of the silyl functional group to the amino groups of the silylated peptide (I) is from 50 to 80%, that is to say, the silyl functional group is introduced to 50 to 80% of the total amount of the amino nitrogen and the imino nitrogen. If the introduction rate of the silyl functional group is less than 50%, there is a possibility that the properties based on the silyl compounds are not sufficiently exhibited. If the introduction rate is more than 80%, there is a possibility that the hydrophobic property is increased to decrease the hydrophilic property, so the storage stability may be deteriorated.

In the silylated peptide shown by the formula (I), $R^1$, $R^2$ and $R^3$ are specified as methyl group or hydroxyl group so that the silylated peptide can maintain its water solubility. Also, A in the silyl functional group is specified as methylene, propylene, $-CH_2OCH_2CH(OH)CH_2-$ or $-(CH_2)_3OCH_2CH(OH)CH_2-$ in order to secure the water solubility and the stability.

In the silylated peptide shown by the formula (I), $R^4$ is a residue of a basic amino acid having an amino group at the end of a side chain wherein the terminal amino group and the group $-CH(NH_2)COOH$ are excluded from the basic amino acid. Examples of the basic amino acid having an amino group at the end of a side chain are, for instance, lysine, arginine, histidine, hydroxylysine, and the like. Also, $R^5$ is a side chain of an amino acid other than the above-mentioned basic amino acid. Examples of such other amino acid are, for instance, glutamic acid, aspartic acid, alanine, serine, threonine, valine, methionine, leucine, isoleucine, tyrosine, phenylalanine, and the like.

In the silylated peptide shown by the formula (I), m is from 0 to 100, preferably from more than 0 to not more than 10 ($0<m\leq10$), and n is from 0 to 100, preferably from 2 to 40 and m+n is from 1 to 100, preferably from 2 to 100, more preferably from 3 to 50. If m is more than the above range, the number of molecules of the silyl compound bonding to the amino acid in the side chains increases, so the sorption action to the hair or skin that the peptide originally possesses is decreased. If n is more than the above range, the proportion of the silyl functional group portion to the peptide portion is small, so the effects based on the silyl compound cannot be sufficiently exhibited. If the sum of m and n (m+n) is more than the above range, the sorption to be exhibited as the peptide is decreased as compared with a low molecular weight peptide, and further, the silylated peptide becomes easy to coagulate during the storage to decrease the storage stability required for cosmetics. The above-mentioned m, n and m+n are theoretically an integer. However, in case that the peptide portion of the silylated peptide is derived from a hydrolyzed peptide as mentioned after, since the hydrolyzed peptide is obtained in the form of a mixture of those having a different molecular weight, in almost all cases the measured values for m and n are average values. The peptide which constitutes the peptide portion in the silylated peptide (I) encompasses an amino acid, a peptide, and an ester of an amino acid or a peptide, as explained after in detail.

[Action of Silylated Peptide onto Hair and Skin]

If the silylated peptide (I) is incorporated into hair cosmetics, it serves to impart luster and moisture to hair, to smooth hair, to improve the combability of hair and to prevent generation of split hair and worn hair. For example, in case of imparting elasticity to hair by a silicone oil as conventionally conducted, it is required to use a high molecular weight silicone oil. However, the high molecular weight silicone oil once stuck to hair is difficult to come out and, therefore, it becomes difficult to conduct a chemical treatment such as permanent waving, bleaching or hair dyeing. In addition, the sorption action of peptides and cationized polymers onto hair is decreased.

In contrast, since the silylated peptide (I) is composed of low molecular weight silyl functional groups bonded to a peptide portion and accordingly is sorbed to hair according to the sorption mechanism of a usual peptide, it is reversibly removable from the hair by rinsing with the detergent containing no peptide, thus causing no trouble as mentioned above.

Further, it is known that a high molecular weight silicone oil can be sorbed by a non-damaged hair, namely a hair predominant in a hydrophobic property, but is difficult to be sorbed by a hair which has had a hydrophilic property as a result of exposure of a hydrophilic group onto the surface by damage. In this respect, in case of the silylated peptide, the silyl functional groups can be sorbed by a damaged hair through the peptide portion so as to restore the strength and feeling of touch of damaged hair.

If the silylated peptide (I) is incorporated into skin cosmetics, it is sorbed by a skin to impart luster and moisture to the skin, thus smoothing the skin.

Moreover, since the silylated peptide has a peptide portion and a water-insoluble silyl compound portion in a molecule, the silyl compound is sorbed by a hair or skin in an improved efficiency, unlike a conventional base material of a mixture type of a silicone oil and a polypeptide. In addition, since the silylated peptide has a good emulsifying stability, it can also be used as an emulsifier, an emulsion stabilizer or a penetrating agent.

[Peptides]

The peptides for constituting the peptide portion of the silylated peptide (I) include an amino acid, a peptide, and an ester of an amino acid or a peptide.

Examples of the amino acid used for forming the peptide portion of the silylated peptide are, for instance, alanine, glycine, valine, leucine, isoleucine, proline, phenylalanine, tyrosine, serine, threonine, methionine, arginine, histidine, lysine, asparagine, aspartic acid, glutamine, glutamic acid, cystine, cysteine, cysteic acid, tryptophan, hydroxyproline, hydroxylysine, O-phosphoserine, citrulline, and the like.

As the peptide used for forming the peptide portion of the silylated peptide, there are mentioned natural peptide, synthetic peptide, a peptide obtained by partially hydrolyzing a protein with an acid, an alkali or an enzyme (this peptide being hereinafter referred to as "hydrolysis peptide"), and the like.

Examples of the natural peptide are, for instance, glutathione, bacitracin A, insulin, glucagon, oxytocin, vasopressin, and the like. Examples of the synthetic peptide are, for instance, polyglycine, polylysine, polyglutamic acid, polyserine, and the like.

Examples of the protein source for the hydrolysis peptide are, for instance, collagen (including its modification product gelatin), keratin, silk fibroin, sericin, casein, conchiolin, yolk protein and albumen protein of eggs such as fowl egg and other proteins derived from animals, proteins derived from vegetables such as soybean, beer cake, corn, rice (rice bran) and potatoes, proteins derived from microorganisms, e.g. yeast proteins separated from yeasts such as yeasts belonging to genera Saccharomyces, Candida and Endomycopsis, or yeasts such as so-called beer yeasts and sake yeasts, and proteins separated from fungi (Basidiomycetes) or chlorella, and other proteins.

The hydrolysis peptides used in the silylation are obtained by hydrolyzing proteins as mentioned above with an acid, an alkali or an enzyme. The degree of polymerization of an amino acid in the hydrolysis peptides can be adjusted to preferable one within the range of 1 to 100 by suitably selecting the amount of the acid, alkali or enzyme used, the reaction temperature, the reaction time and the like.

Examples of the acid used in the acid hydrolysis of proteins are, for instance, an inorganic acid such as hydrogen chloride, sulfuric acid, phosphoric acid, nitric acid or hydrobromic acid, and an organic acid such as acetic acid or formic acid.

Examples of the alkali used in the alkali hydrolysis of proteins are, for instance, sodium hydroxide, potassium hydroxide, lithium hydroxide, barium hydroxide, sodium carbonate, potassium carbonate, lithium carbonate and other inorganic alkaline substances.

Examples of the enzyme used in the enzymatic hydrolysis of proteins are, for instance, an acidic proteolytic enzyme such as pepsin, proctase A or proctase B, and a neutral or alkaline proteolytic enzyme such as papain, bromelyn, thermolysin, trypsin, pronase or chymotrypsin. Neutral or alkaline proteolytic enzymes produced by microorganisms, e.g. subtilisin and Slaphylococcus protease, can also be used.

The ester of an amino acid or a peptide, which can be used for forming the peptide portion of the silylated peptide (I), includes for instance esters of the amino acid or peptide as exemplified above at its carboxyl group with a hydrocarbon alcohol having 1 to 20 carbon atoms, e.g. alkyl esters such as methyl, ethyl, propyl, isopropyl, butyl, lauryl, cetyl, 2-ethylhexyl, 2-hexyldecyl and stearyl esters.

In case of incorporating the silylated peptide (I) of the present invention into hair cosmetics and skin cosmetics, it is preferable from the viewpoints of the sorption of peptide to hair or skin, the film forming property and the penetrating property that the degree of polymerization of amino acid is from 2 to 100, especially from 3 to 50.

[Silyl Compounds]

The silyl compounds shown by the formula (III) or (IV) are used as a silylating agent in the silylation of the peptides mentioned above. The silyl compounds (III) or silyl compounds (IV) are commercially available from silane coupling agents put on the market, e.g. TSL8390, TSL8219, TSL8395, TSL8326, TSL8325, TSL8320, TSL8355 and TSL8035 (trade mark, products of Toshiba Silicone Kabushiki Kaisha); SH6040 and SH6076 (trade mark, products of Toray Dow Corning Silicone Kabushiki Kaisha); KMB402, KMB403 and KMB703 (trade mark, products of Shin-Etsu Chemical Co., Ltd.); A-143 (trade mark, product of Nippon Unicar Kabushiki Kaisha); and the like. Representative examples of the compounds (III) and (IV) are, for instance, γ-chloropropyltrimethoxysilane, γ-glycidyloxypropyltrimethoxysilane, γ-glycidyloxypropylmethyldiethoxysilane, and the like.

In the formulas (III) and (IV), the groups $R^6$, $R^7$ and $R^8$ are specified as methyl group, methoxy group, ethoxy group, hydroxyl group or a halogen atom so that they remain as methyl group or hydroxyl group as a result of the reaction with the peptides in water, whereby the obtained silylated peptide has a water solubility.

[Synthesis of Silylated Peptide]

The reaction of the peptides (II) with the silyl compounds (III) or (IV) is carried out in such a manner that the silyl compounds are first stirred in water at a temperature of 30° to 50° C. for 5 to 20 minutes to convert the alkoxyl group or halogen atom attaching to the silicon atom into hydroxyl group, and the thus treated silyl compounds are then added dropwise to the peptides, thus proceeding with the reaction by contacting them.

In the above reaction, the peptides are preferably used in the form of an aqueous solution having a concentration of about 30 to about 50% by weight. It is preferable that the dropwise addition of the treated silyl compounds is carried out over 30 minutes to 5 hours.

In case of using the silyl compound (III), a hydrogen halide is produced by the reaction to lower pH of the reaction mixture. Therefore, it is preferable to maintain the pH of the reaction system at 8 to 11, especially 9 to 10, by adding dropwise an aqueous solution of an alkali such as sodium hydroxide or potassium hydroxide simultaneously with the reaction. Also, in case of using the silyl compound (IV), no pH drop owing to the reaction occur if the silyl group does not contain a halogen atom. However, since the reaction proceeds on a basic side, it is preferable to maintain the reaction system at a pH of 8 to 11, especially 9 to 10.

The reaction proceeds at ordinary temperature, but the rate of reaction increases with raising the temperature. On the other hand, if the reaction system is raised to a high temperature under a high pH condition, the hydrolysis of the silyl compound is accelerated. Therefore, the reaction temperature is preferably at the highest 70° C., especially from 40° to 60° C.

The progress and completion of the reaction can be confirmed by measuring the amount of amino nitrogen in the peptide subjected to the reaction according to a Van Slyke method.

After the completion of the reaction, the reaction mixture is neutralized, optionally concentrated, and purified by means of an ion exchange resin, a dialysis membrane, electrodialysis, gel filtration or ultrafiltration. The thus purified silylated peptide in the form of a liquid may be powdered, as occasion demands, and is incorporated in the form of a liquid or a powder into hair cosmetics and skin cosmetics.

[Uses of Cosmetic Base Material Comprising Silylated Peptide]

The base material for cosmetics comprising the silylated peptide (I) according to the present invention is applicable to various cosmetics, e.g., shampoo, hair rinse, split hair coating, first and second solutions for permanent waving treatment, hair cream, hair conditioner, set lotion, hair color or hair dye, hair treatment rinse, liquid hair dressing, hair pack, hair tonic and other hair cosmetics, toilet water such as astringent lotion or emulsion, after-shaving lotion, shaving foam, various creams such as vanishing cream, cleansing cream, emollient cream, moisture cream, hand cream and rolling massage cream, depilatory, face pack, emulsion, cleaning preparation, body shampoo, various soaps, makeups, anti-suntan and anti-sunburn preparations, and other known cosmetics.

Preferably, the base material of the present invention, namely the silylated peptide (I), is used in a concentration of about 0.1 to about 30% by weight, especially about 1 to about 20% by weight, in a cosmetic. If the content of the silylated peptide (I) in a cosmetic is less than the above range, effects of imparting luster and moisture to hair, effect of protecting hair and effect of improving the combability of hair are not sufficiently exhibited. Even if the content of the silylated peptide (I) is used in an amount of more than the above range, further increase in these effects based on the increase in the content beyond the above range is not obtained, and rather the sorption of excess silylated peptide causes the hair or skin sticky.

In the preparation of the cosmetics as mentioned above, the silylated peptide (I) can be used as the cosmetic base material with various components. Representative examples thereof are, for instance, an anionic surfactant, e.g. an alkyl sulfate such as sodium lauryl sulfate or lauryl sulfate ethanolamine, a polyoxyethylene alkyl ether sulfate such as polyoxyethylene(2) lauryl ether sulfate triethanolamine or a sodium polyoxyethylene(3) alkyl ether sulfate wherein the alkyl group is one having 11 to 15 carbon atoms or a mixture thereof, an alkylbenzene sulfonate such as sodium laurylbenzene sulfonate or laurylbenzene sulfonate triethanolamine, a polyoxyethylene alkyl ether acetate such as polyoxyethylene(3) tridecyl ether acetate, an N-acylamino acid salt such as sodium salt of coconut oil fatty acid L-glutamate or sodium salt of coconut oil fatty acid sarcosine, an acylated hydrolyzed protein or its salt obtained by acylation of the hydrolysis product of proteins derived from animals or vegetables such as collagen, keratin, fibroin, casein, soybean, wheat or corn, or of the hydrolysis product of proteins derived from microorganisms such as yeasts or fungi, with a fatty acid having 8 to 20 carbon atoms, sodium hardened coconut oil fatty acid glycerol sulfate, a sodium polyoxyethylene(8 to 10) alkyl ether phosphate wherein the alkyl group has 12 to 15 carbon atoms, sodium polyoxyethylene cetyl ether phosphate, sodium coconut oil fatty acid methyl taurate, or sodium coconut oil fatty acid isethionate; a cationic surfactant such as distearyl dimethylammonium chloride or stearyltrimethylammonium chloride; an amphoteric surfactant such as $2\text{-}C_{12-15}$ alkyl-N-carboxymethyl-N-hydroxyethylimidazolium betaine, sodium undecylhydroxyethylimidazolium betaine, N-coconut oil fatty acid acyl-L-arginine ethyl-DL-pyrrolidone carboxylic acid salt, coconut oil fatty acid amide propyl betain or $N\text{-}C_{12-18}$ alkyldimethylaminoacetic acid betaine; a non-ionic surfactant such as polyoxyethylene(7) $C_{12-14}$ alkyl ether, polyoxyethylene oleyl ether, polyoxyethylene nonylphenyl ether, an alkyl glycoside or an alkyl polyglycoside; a cationic, amphoteric or anionic synthetic polymer such as cationized cellulose or cationized hydroxyethylcellulose; a thickener such as isostearic acid diethanolamide or lauric acid diethanolamide; a wetting agent such as an animal or vegetable extract, polysaccharide or its derivative, propylene glycol, 1,3-butylene glycol or glycerol; a lower alcohol such as ethanol, methanol or propanol; an amino acid such as sodium L-asparate, DL-alanine, glycine, L-arginine or L-cysteine; and the like. Other components or additives can be suitably incorporated into cosmetics so long as the effects of the present invention are not impaired.

If the silylated peptide (I) is used in combination with a silicone oil such as a linear or cyclic dimethyl polysiloxane, methylphenyl polysiloxane or amino-modified silicone oil, it serves to improve the emulsifying stability of the silicone oils and to enhance the actions of the silicone oils.

[Hair treating composition containing silylated peptide]

If the silylated peptide (I) is incorporated into a hair treating composition such as a hair rinse, a hair conditioner or a hair treatment, it can simultaneously exhibit both excellent properties based on the silyl functional group portion such as extensibility, friction-reducing property, luster or gloss-imparting action and water repellency-imparting action and excellent properties based on the peptide portion such as sorption action to hair, hair volume-increasing action accompanied by the improved sorption, impartment of elasticity, protective action by film formation and hygroscopicity, since it has the silyl functional group portion and the peptide portion as apparent from the chemical structural formula thereof. The hair treating compositions according to the present invention are explained below in detail in comparison with hair treating compositions containing no silylated peptide.

In conventional hair treating compositions such as hair rinse, hair conditioner, hair treatment and the like, a cationic surfactant has been used in combination with a silicone oil in order to soften the hair, to improve the combability of the hair and to prevent the electrification of the hair on the basis of the cationic surfactant, and in order to smooth the hair, to impart luster to the hair and to prevent formation of split hair owing to combing on the basis of the silicone oil.

However, such an idea only improves the surface physical properties of a hair, and has the disadvantages that the protein component of the hair is eluted by hair washing to damage the hair, and as a result, when the hygroscopicity of the hair is decreased or when the hair dries up crisp, it is impossible to eliminate these problems. Also, a high molecular weight silicone oil is easy to be sorbed by a little damaged hair, namely a hair having a strong hydrophobic property, but is hard to be sorbed by a damaged hair, namely a hair which has become strongly hydrophilic as a result of hydrophilic groups exposing to the surface by damage. Therefore, the properties of the silicone oil cannot be sufficiently exhibited to damaged hairs. Further, the silicone oil is a lipophilic compound and, therefore, it is necessary to prevent its separation by means of an emulsifier when incorporated into aqueous hair rinse or hair treatment.

In contrast, since the silylated peptide (I) has the silyl functional group portion and the peptide portion as mentioned above, it can simultaneously exhibit the above-mentioned excellent properties based on the silyl functional group portion and the peptide portion. Moreover, since peptides have a good sorption property to damaged hairs, the silylated peptide (I) enables to sorb the silyl functional group onto the damaged hairs by which high molecular weight silicone oils are hard to be sorbed, through the peptide portion, whereby it is possible to improve the feeling of touch of damaged hairs and to contribute to restoring the strength of hairs.

Also, the high molecular weight silicone oils have the defect that the silicone oils once stuck to a hair is hard to come out, whereby chemical treatment of the hair such as permanent waving, breaching or dyeing is made difficult and the sorption action of a peptide or a cationic polymer to the hair is decreased. In contrast, since the silylated peptide (I) is composed of a peptide portion and a low molecular weight silyl functional group portion bonded to the peptide portion and can be sorbed by a hair according to the sorption mechanism of usual peptides, it is reversibly removable from the hair by rinsing with a detergent containing no peptide, so no trouble as mentioned above occur.

Therefore, when a hair treating composition is prepared by using a cationic surfactant in combination with the silylated peptide (I), the obtained composition has excellent properties based on the silylated peptide to impart luster and moisture to a hair, to smooth the hair, to improve the combability of the hair, to prevent generation of split hair and worn hair, to restore the strength of damaged hair and to prevent the cationic surfactant from damaging the hair owing to excess adsorption of the surfactant. Further, the cationic surfactant incorporated therein is adsorbed by the hair to soften the hair, to prevent electrification of the hair and to improve the combability of hair.

A treating composition used in PPT (polypeptide) treatment which is mainly practiced in a middle step of permanent waving treatment or dyeing treatment, usually contains a protein hydrolysis product in a high concentration of 20 to 50% by weight. The incorporation of a high concentration of the protein hydrolysis product is required in order to raise the effect of restoring a damaged hair, since the permanent waving treatment and the dyeing treatment accompany a chemical change to give a heavy damage to the hair and since the PPT treating composition is washed away by using a shampoo within a short period of time after the treatment. It has hitherto been attempted to incorporate a component capable of raising the recovering effect for a damaged hair into this PPT treating agent. However, a high molecular weight silicone oil cannot be used in the PPT treating agent, since the silicone oil once adhered to the hair is hard to remove, thus resulting in difficulty of chemical treatment of hair.

In contrast, the silylated peptide (I) is soluble in water and, in addition, is sorbed by a hair according to a sorption mechanism of peptides and, therefore, it is easily removable by usual washing with a shampoo. Further, since the silylated peptide has a structure such that silyl functional groups are bonded to an amino acid or a peptide, it does not form a polymer film as formed by a silicone oil and, therefore, there is no trouble such that it becomes difficult to wave a hair in permanent waving treatment or a hair dyeing effect in dyeing treatment is deteriorated.

It is preferable that the content of the silylated peptide (I) in the hair treating composition is from 0.1 to 20% by weight, especially from 0.5 to 15% by weight. If the content of the silylated peptide (I) is less than the above range, the effects such as luster and moisture impartment, hair protection, improvement of combability and prevention of excess adsorption of cationic surfactants are not sufficiently exhibited. Even if the silylated peptide (I) is used in an amount exceeding the above range, no further improvement is obtained.

In incorporating the silylated peptide (I) into the hair treating composition, the silylated peptide may be used alone or in admixture thereof.

In the hair treating composition, the cationic surfactant is used in order to raise the hair conditioning actions of the composition such as actions to soften and smooth the hair and action to prevent electrification of the hair.

Examples of the cationic surfactant are, for instance, stearyltrimethylammonium chloride, cetyltrimethylammonium chloride, cetostearyltrimethyl-ammonium chloride, stearylbis(diethylene glycol)-hydroxyethylammonium chloride, behenyltrimethylammonium chloride, distearyldimethylammonium bromide, stearyldimethylbenzylammonium chloride, behenyltrimethylammonium bromide, cetyltrimethylammonium iodide, oleylbenzyldimethylammonium chloride, oleylbis[polyoxyethylene(15)]methylammonium chloride, tri[polyoxyethylene(5)]stearylammonium chloride, polyoxypropylenemethyldiethylammonium chloride, mink oil fatty acid amido propyl-diethylhydroxyethylammonium chloride, an alkylpyridinium salt, γ-gluconeamidopropyl-dimethylhydroxyethylammonium chloride, and the like. The cationic surfactant may be used alone or in admixture thereof.

It is preferable that the content of the cationic surfactant in the hair treating composition is from 0.2 to 5% by weight, especially from 0.5 to 2% by weight. If the content of the cationic surfactant is less than the above range, the effects of the surfactant are not sufficiently exhibited. If the content is more than the above range, the cationic surfactant is adsorbed too much by the hair, so the hair is extremely softened to deteriorate the feeling of touch and there is a possibility of causing elution of a protein component of hair, lowering the hygroscopicity of hair or making hair dry up crisp.

The hair treating composition according to the present invention is prepared by dissolving the essential components, namely the silylated peptide (I) and the cationic surfactant, in water or a mixture of water and a suitable solvent. The composition may further contain other components or additives such as fats and oils, active agent, synthetic polymer, thickener, peptide obtained by hydrolysis of proteins or its derivative, wetting agent, alcohol, amino acid, silicone oil, and the like.

[Shampoo containing silylated peptide]

The silylated peptide (I) is soluble in water, and has both a silyl functional group portion and a peptide portion as apparent from the structural formula. Therefore, if the silylated peptide (I) is incorporated into a shampoo, both excellent properties based on the silyl functional group portion such as extensibility, friction-reducing property, luster or gloss-imparting property and water repellency-imparting property and excellent properties based on the peptide portion such as sorption action to hair, hair volume-increasing action, strongness or vividness-imparting action, and protective action and hygroscopicity by film formation can be simultaneously exhibited without causing separation of the silylated peptide from surfactants. Thus, if the silylated peptide (I) of the present invention is incorporated into shampoos, it provides a soft touch feeling to foams upon hair washing, smoothes the hair to improve the combability of the hair and prevents generation of split hair and worn hair. The shampoo composition according to the present invention is explained in detail below in comparison with a shampoo containing no silylated peptide (I).

Shampoos which have hitherto been generally used, are composed of one or more of surfactants as a main component, e.g. an anionic surfactant such as an alkyl sulfate or a polyoxyethylenealkyl sulfate, a non-ionic surfactant such as a polyoxyethylene alkyl ether or a fatty acid alkylolamide, and an amphoteric surfactant such as an alkyl betain or an alkylamine oxide. There are also proposed shampoos to which a cationic surfactant is added in order to provide a soft and wet feeling to a hair.

However, if a hair is washed with shampoos containing these surfactants, the sebum and other oil components present in the surface of the hair are washed away, whereby the luster and moisture of the hair are lost and the hair is dried up crisp to extremely deteriorate the feeling of touch of the hair, and also the combability and brushing property of the hair are deteriorated, resulting in cause of generating split hair and worn hair.

For such reasons, it may be possible, as proposed for other hair cosmetics, to incorporate a silicone oil and a polypeptide into a shampoo for the purpose of exhibiting the properties of the silicone oil such as extensibility, luster or gloss impartment to hair and hair protection by water repellency impartment with the properties of the polypeptide such as sorption action to hair and actions to protect and to impart hygroscopicity to the hair by film formation on the hair. However, since the silicone oil is a hydrophobic (lipophilic) substance whereas the polypeptide is a hydrophilic substance, both are hardly compatible with each other. If they are used in combination, the obtained products are poor in emulsion stability and separation is easy to occur to impair the commodity value as shampoo. Also, the polypeptide is hard to attach to a portion to which the silicone oil has attached in advance of the polypeptide and vice versa, thus the properties of the both cannot be sufficiently exhibited.

In contrast, the silylated peptide (I) is soluble in water and is composed of a silyl functional group portion and a peptide portion. Therefore, if the silylated peptide (I) is incorporated into shampoos, it can simultaneously exhibit excellent properties based on the silyl functional group portion and the peptide portion as mentioned above. Thus, if the silylated peptide (I) is incorporated into shampoos, it provides a soft touch feeling to foams produced in washing a hair, smoothes the washed hair to improve the combability of the hair and prevents generation of split hair and worn hair.

Further, if a shampoo is prepared by using the silylated peptide (I) in combination with a cationic surfactant and at least one non-cationic surfactant selected from the group consisting of an anionic surfactant, a non-ionic surfactant and an amphoteric surfactant, hair conditioning effects such as softening and smoothing the hair are further improved in addition to the above-mentioned effects. Also, when an amino acid type anionic surfactant or an acylation product of a protein-derived peptide or its salt is used as the above-mentioned non-cationic surfactant, the damage of hair is decreased in addition to the above effects.

Preferably, the content of the silylated peptide (I) in a shampoo is from 0.05 to 10% by weight, especially 0.2 to 5% by weight. If the content of the silylated peptide is less than the above range, the effects based on the silylated peptide are not sufficiently obtained. Even if the silylated peptide is used in a concentration exceeding the above range, substantial further increase in the effects is not obtained by increasing the amount. In the preparation of shampoos, the silylated peptide (I) may be used alone or in admixture thereof.

The shampoos according to the present invention can be prepared in a conventional manner excepting the use of the silylated peptide (I).

For example, as the surfactants to be used as the main component of the shampoo, there can be used various surfactants as conventionally used, e.g. one or more of anionic surfactants, amphoteric surfactants, non-ionic surfactants and cationic surfactants. It is preferable that the content of these surfactants in the shampoo is from 2 to 25% by weight, especially about 5 to about 15% by weight.

Examples of the anionic surfactant used in the shampoo are, for instance, alkyl sulfates, polyoxyethylene alkyl ether sulfates, alkylbenzene sulfonates, alkylsulfosuccinates, alkyl ether phosphates, and the like.

Examples of the amphoteric surfactant are, for instance, betaine type surfactants, imidazoline type surfactants, and the like. Examples of the non-ionic surfactant are, for instance, polyoxyethylene type surfactants, alkylpolyglycoside type surfactants, and the like.

The shampoos according to the present invention are prepared by mixing the essential components, namely the silylated peptide (I) and the surfactant, with water or a mixture of water and a suitable solvent. In particular, when a combination of at least one non-cationic surfactant selected from the group consisting of anionic, non-ionic and amphoteric surfactants with a cationic surfactant is used as the surfactant to be mixed with the silylated peptide (I), hair conditioning effects such as softening and smoothing the hair are further increased in addition to the effects as produced by the silylated peptide. Further, when an amino acid-based anionic surfactant, an acylation product of a protein-derived peptide or a salt of the acylation product is used as the above-mentioned non-cationic surfactant, favorable effects such as reduction of damage of hair are further produced in addition to the effects mentioned above.

That is to say, the amino acid type anionic surfactant and the acylation product of protein-derived peptide or its salt act as the main component exhibiting a detergency, and moreover they are low stimulative and have a less action of denaturing proteins. On the other hand, the cationic surfactant is adsorbed by the hair to raise the hair conditioning action such as softening and smoothing the hair. Further, the silylated peptide (I) prevents excess adsorption of the cationic surfactant to the hair, thus preventing the hair from suffering damage owing to excess adsorption of the cationic surfactant.

The amino acid type anionic surfactant and the acylation product of proten-derived peptide or its salt serve as the main component exhibiting the detergency in the shampoo. A hair is constituted by a keratin protein which is a polymer of amino acids. From this point of view, the use of the amino acid type anionic surfactant or the acylation product of protein-derived peptide or its salt is advantageous since they are low in protein denaturing action and stimulation.

Examples of such an amino acid type anionic surfactant are, for instance, lauroyl sarcosine, myristoyl sarcosine, palmitoyl sarcosine, stearoyl sarcosine, behenoyl sarcosin, coconut oil fatty acid methyl taurate, N-myristoyl methyl taurate, N-stearoyl methyl taurate, N-behenoyl methyl taurate and their salts, monosodium lauroyl-L-glutamate, monosodium N-cocoyl-L-glutamate, monosodium N-stearoyl-L-glutamate, N-palmitoyl-L-glutamic acid monoethanolamine, disodium N-palmitoyl-L-glutamate, sodium N-cocoyl-N-methyl-β-alanine, sodium N-lauroyl-N-methyl-β-alanine, sodium N-myristoyl-N-methyl-βalanine, sodium N-cocoyl-aminopropionate, and the like.

Examples of the acylation product of protein-derived peptide or its salt are, for instance, an acylated peptide or its salt represented by the formula (V):

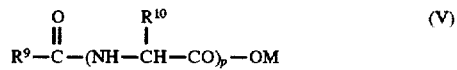

$$R^9-\overset{O}{\underset{\|}{C}}-(NH-\overset{R^{10}}{\underset{|}{CH}}-CO)_p-OM \qquad (V)$$

wherein $R^9$ is an alkyl group having 7 to 21 carbon atoms or an alkenyl group having 7 to 21 carbon atoms, $R^{10}$ is a side chain of an amino acid, M is H, Na, K, NH3 or an onium of an organic alkanol amine such as monoethanolamine, diethanolamine, triethanolamine, 2-amino-2-methyl-1-propanol or 2-amino-2-methyl-1,3-propanediol, and p is from 1 to 100.

Examples of the protein-derived peptide in the acylated peptide or its salt represented by the formula (V) are, natural peptides, synthetic peptides and peptides obtained by hydrolysis of various proteins, such as those exemplified as the peptides for the silylated peptide (I).

In the formula (V), p is from 1 to 100, especially from 3 to 3 0. The value p is theoretically an integer, but in case that the peptide portion is one derived from a hydrolysis peptide, the hydrolysis peptide is obtained in the form of a mixture of peptides having a different molecular weight and, therefore, the measured value p is obtained as an average value.

Examples of the acylated peptide or its salt (V) are, for instance, if exemplified with respect to those prepared from a collagen-derived peptide, potassium undecylenoyl-hydrolyzed collagen, sodium lauroyl-hydrolyzed collagen, potassium cocoyl hydrolyzed collagen, sodium cocoyl hydrolyzed collagen, triethanolamine cocoyl hydrolyzed collagen, cocoyl hydrolyzed collagen, potassium myristoyl-hydrolyzed collagen, isostearoyl-hydrolyzed collagen, and the like. With respect to protein-derived peptides other than the collagen-derived peptide, there are exemplified the acylated peptides or their salts analogous to the acylation products of collagen-derived peptide exemplified above.

The amino acid-based anionic surfactants and the acylated peptides or their salts may be used alone or in admixture of one or more of them.

Preferably, the content of the amino acid-based anionic surfactant and/or the acylated peptide or its salt in a shampoo is from 0.1 to 25% by weight, especially from 5 to 15% by weight. If the content is less than the above range, the detergency is decreased. Even if the amino acid-based anionic surfactant or the acylated peptide or its salt is used in an amount exceeding the above range, no marked increase in effects is observed.

In the shampoo according to the present invention, the cationic surfactant is adsorbed by a hair to soften the hair and serves to impart a luster to the hair as well as the silylated peptide (I). As the cationic surfactant, those exemplified above can be used. The cationic surfactants may be used alone or in admixture thereof.

It is preferable that the content of the cationic surfactant in the shampoo is from 0.2 to 5% by weight, especially from 0.5 to 2.5% by weight. If the content of the cationic surfactant is less than the above range, its effects are not sufficiently exhibited. If the content is more than the above range, the cationic surfactant is absorbed too much by the hair, thus deteriorating the feeling of touch such as extremely softening the hair.

In case of using the amino acid-based anionic surfactant or the acylated peptide or its salt and the cationic surfactant in combination with the silylated peptide too, shampoos are prepared by adding them to water or a mixed solvent of water and an organic solvent.

So long as the desired effects are not impaired, the shampoos according to the present invention may contain other components or additives, such as various synthetic polymers, thickener, fats and oils, extracts from animals and vegetables, wetting agent, alcohols, anti-dandruff agent, hydrolysis products of proteins derived from animals and their esters or their quaternary ammonium derivatives, and other known additives for shampoos.

[Permanent Waving First Solution Containing Silylated Peptide]

Since the silylated peptide (I) is soluble in water and is composed of a silyl functional group portion and a peptide portion, the silylated peptide, if incorporated into a permanent waving first solution, is sorbed by a hair through the sorption action of the peptide portion to prevent the hair from suffering damage by a permanent waving treatment, to restore a damaged hair and to impart moisture to the hair. Since the silyl functional group portion is also sorbed by the hair through the peptide portion, it is possible to impart a desired good wave to the hair without hindering the permanent waving treatment. The permanent waving first solution according to the present invention is explained in detail below in comparison with that containing no silylated peptide.

A conventionally used waving lotion or permanent waving first solution is an aqueous solution containing as a main component a reducing agent, such as thioglycolic acid or cysteine, to which a basic substance such as ammonia, monoethanolamine or triethanolamine is added to adjust to pH 8 to 10. An aqueous solution of an oxidizing agent such as sodium bromate or hydrogen peroxide is used as a second solution. The first solution is applied to a wound or curled hair, whereby disulfide linkages of cystine included in keratin which is a constituent protein of the hair, are cleaved to produce mercapto groups by reduction, and the second solution is then applied to the cured hair treated by the first solution, thereby oxidizing the mercapto groups to produce disulfide linkages again at new positions, thus fixing the wave.

However, in case of the permanent treatment using such waving lotions, the disulfide linkages in cystine severed by a reducing agent of the first solution are not always restored completely to the former state by oxidization by means of the second solution so as to regenerate cystine. A part of mercapto groups produced by the treatment with the first solution undergo excess oxidation by means of the second solution, thus causing side reactions such as reaction with mercapto groups of thioglycolic acid or cysteine present in the hair to produce disulfide linkages. As a result, there occur damages such that a part of keratin protein of the hair is eluted or other portions of the hair receive physical or chemical changes. Thus, not only a feeling of physical disorder or a dry crisp feeling is given to the hair, but also the hair is markedly damaged.

For such a reason, it is proposed to incorporate a silicone oil into the permanent waving first solution in order to reduce a dry crisp feeling of the hair after the permanent waving treatment, to improve the combability or to restore the strength of the damaged hair. However, although the dry crisp feeling is reduced since the silicone oil forms a film on the hair, the silicone oil has no fundamental restoration action onto a hair damaged by elution of keratin protein from the hair. The silicone oil also has problems that not only it is not possible to impart moisture to the hair, but also it becomes difficult to impart wave to the hair since the silicone oil forms a film on the hair. Further, the silicone oil is generally a liophilic (hydrophobic) substance, and it is easy to be sorbed by a less damaged hair which has a strong hydrophobic property. However, the silicone oil is hard to be sorbed by a damaged hair which has an increased hydrophilic property as a result of exposure of hydrophilic groups onto the surface by damage and, therefore, the sorption of the silicone oil to a hair greatly damaged by permanent waving treatment is not so expectable. Further, since the permanent waving solution is generally an aqueous solution, an emulsifier must be incorporated in order to emulsify the silicone oil. The silicone oil may cause separation during storage depending on the storage conditions, thus a permanent waving first solution incorporated with a silicone oil also has a problem of being poor in storage stability.

In contrast, since the silylated peptide (I) of the present invention is soluble in water and is composed of a silyl functional group portion and a peptide portion, the silylated peptide, if incorporated into a permanent waving fitst solution, is sorbed by a hair through the sorption action of the peptide portion and serves to prevent the hair from suffering damage by the waving treatment, to restore a damaged hair and to impart moisture to the hair. Since the silyl functional group portion is also sorbed by the hair through the peptide portion, it is possible to impart a desired good wave to the hair without hindrance from imparting wave to the hair.

When a cationic surfactant is incorporated into the permanent waving first solution together with the silylated peptide, a softness is imparted to the hair and the combability of the hair and the waving efficiency are improved, in addition to the effects mentioned above.

It is preferable that the content of the silylated peptide (I) in the permanent waving first solution is from 0.1 to 15% by weight, especially from 1 to 5% by weight. If the content of the silylated peptide in the first solution is less than the above range, there are not sufficiently exhibited an effect of protecting the hair to prevent the hair from suffering damage, an effect of imparting luster and moisture to the hair and an effect of preventing excess adsorption of a cationic surfactant. Even if the silylated peptide is used in a concentration exceeding the above range, no further increase in the effects is obtained and the hair rather becomes sticky by excess adsorption of the silylated peptide.

The reducing agent in the permanent waving first solution is used as the main component thereof in order to sever the disulfide linkages of cystine in keratin which is a hair-constituting protein, followed by oxidation to thereby provide a wave to the hair. Examples of the reducing agent used in the permanent waving first solution are, for instance, thioglycolic acid, a salt of thioglycolic acid such as ammonium thioglycolate or thioglycolic acid monoethanolamine, an ester of thioglycolic acid such as glycerol thioglycolate, cysteine, a salt of cysteine such as cysteine hydrochloride or acetyl cysteine, an organic mercaptan compound such as thioglycerol, thiolactic acid, thiomalic acid, cysteamine or cysteamine hydrochloride, a sulfinic acid salt such as sodium sulfite, sodium hydrogensulfite, potassium sulfite or ammonium sulfite, and the like. These reducing agents may be used alone or in admixture thereof.

The content of the reducing agent in the waving first solution is from 1 to 10% by weight, especially from 2 to 8% by weight. If the content of the reducing agent is less than the above range, no satisfactory wave is obtained. If the content is more than the above range, there is a possibility that the disulfide linkages in the hair undergo reduction in excess and elution of protein from the hair becomes marked to result in great damage.

The permanent waving composition according to the present invention used in the first stage of the permanent waving treatment is prepared by adding the essential components, namely a reducing agent and the silylated peptide (I), to water or a liquid composed mainly of water. The silylated peptide (I) may be added to permanent waving first lotions containing a reducing agent which have been already prepared or are being prepared. The reducing agent and the silylated peptide can be added in any order.

So long as the effects of the present invention are not impaired, the permanent waving composition according to the present invention may contain other components such as anti-inflammatory agent, penetrating agent, surfactant, synthetic polymer, thickener, fats and oils, extracts from animals and vegetables, alcohols, hydrolysis products of proteins derived from animals and vegetables, esters and quaternary ammonium derivatives of the hydrolysis products, and other known additives conventionally used for permanent waving compositions.

When a cationic surfactant is included in the permanent waving composition in addition to the reducing agent and the silylated peptide (I), the softness and the combability of hairs are further raised and the waving effect is further improved. That is to say, the cationic surfactant is adsorbed by the hair and serves to soften the hair so as to make it easy to impart a wave to the hair, to improve the combability of the hair and to prevent electrification of the hair. Also, the cationic surfactant forms a film on the hair so as to prevent the silylated peptide penetrated into the hair from being washed away by shampooing or the like, whereby retaining the hygroscopicity of the silylated peptide.

It is preferable that the content of the cationic surfactant in the permanent waving composition is from 0.1 to 5% by weight, especially from 0.2 to 2% by weight. If the content of the cationic surfactant is less than the above range, its effects are not sufficiently obtained. If the content of the cationic surfactant is more than the above range, excessive cationic surfactant is adsorbed by the hair to extremely soften the hair, thus deteriorating the feeling of touch of the hair. Further, there is a possibility that the protein component is eluted from the hair and the hygroscopicity is lowered, thus resulting in dry loose hair.

[Hairdye Composition Containing Silylated Peptide]

If the silylated peptide (I) is incorporated into a hairdye, it is sorbed by the hair through sorption action of the peptide portion thereof, and acts to protect the hair from the hair dyeing and to impart moisture to the hair, and also acts, based on the silyl functional group portion attached through the peptide portion, to smooth the surface of hair and to impart luster or gloss to the hair. Also, since the silylated peptide is sorbed by the hair according to the sorption mechanism of usual peptides, it is possible to perform the hair coloring as desired without hindering the hair coloring treatment. The hairdye composition according to the present invention is explained in detail below in comparison with that containing no silylated peptide.

A temporary hairdye and a permanent hairdye are known as the hairdye, and both are widely used for the purpose of beauty.

An oxidation type hairdye comprising a first agent containing an oxidation dye and a second agent containing an oxidant has been widely used as the permanent hairdye, since various color tones are obtained and the coloring power is excellent. On the other hand, since the temporary hairdye can be washed away by one shampooing, it is also widely used for making up purpose.

However, conventional hairdyes have problems that a hair is markedly damaged by dyeing, resulting in a dry loose hair or deterioration of the combability. For example, an oxidation type hairdye usually contains an alkali in order to facilitate uniform penetration of an oxidation dye such that the pH is as high as 10 or more, and accordingly it has the defects that the hair is easy to be damaged and the protein component in the hair is easy to be eluted, and moreover the hairdye is stimulative.

For such a reason, an acidic hairdye containing no alkali has also been used, but it also has the defects that since a bleaching treatment is conducted by oxidation of the hair in order to destroy melanine in the hair, the hair is easy to be damaged to lose its luster and combability though the degree is not so high as the oxidation type hairdye.

Also, in case of most of the temporary hairdyes, the dyeing is performed by adsorbing a dye to cuticle of the root sheath and, therefore, it is necessary to raise the dyeing effect. For this purpose, the dye concentration is raised or a large amount of a spreading agent or a polymer is added, but this causes problems that the hair after the dyeing becomes hard and, since the combability of the hair is deteriorated, the hair is subject to damage by combing.

Recently, use of an acidic hairdye of shampoo type containing no alkali is increasing. The hairdye of this type contains a penetrating agent such as coconut fatty acid diethanolamide, polyoxyethylene nonylphenyl ether or benzyl alcohol. The damage of hair and the elution of protein component in the hair are easy to occur owing to the penetrating agent, whereby the hair becomes a dry loose hair after the dyeing and the hair becomes hard to comb.

In order to eliminate the problems as mentioned above, it is proposed to incorporate a hydrolysis product of proteins or its derivative or a silicone oil to hairdyes. The protein hydrolysis product or its derivative is useful for imparting moisture to a damaged hair since it is well adsorbed by the damaged hair, but it is not satisfactory in improvement of luster and combability of hair. Also, the silicone oil is useful for reducing a dry feeling of the hair and imparting luster to the hair, since it forms a film on the surface of the hair. However, the silicone oil has no restoration action against damage of the hair owing to elution of protein component from the hair, and it is not possible to impart moisture to the hair. Also, the silicone oil film formed on the hair may hinder a chemical treatment such as bleaching or dyeing. Further, since the silicone oil is usually a hydrophobic substance, it is easy to sorbed by a little damaged hydrophobic hair, but is hard to be sorbed by a hair damaged to expose hydrophilic groups onto the surface, thus having a hydrophilic property. Accordingly, the sorption of the silicone oil to a hair greatly damaged by dyeing treatment is not so expectable. Further, since the silicone oil may cause separation in aqueous hairdyes, it is not suited for use in aqueous hairdyes.

In contrast, since the silylated peptide (I) of the present invention is soluble in water and is composed of a silyl functional group portion and a peptide portion, the silylated peptide, if incorporated into a hairdye, is sorbed by a hair through the sorption action of the peptide portion and serves to protect the hair from the dyeing treatment and to impart moisture to the hair, and it also serves, based on the silyl functional group portion sorbed by the hair through the peptide portion, to smooth the surface of the hair and to impart luster to the hair. Also, since the silylated peptide is sorbed according to the sorption mechanism of usual peptides, it is possible to perform the hair dyeing as desired without hindering the hair dyeing treatment.

It is preferable that the content of the silylated peptide (I) in the hairdye composition is from 0.1 to 15% by weight, especially from 0.5 to 10% by weight. If the content of the silylated peptide in the hairdye composition is less than the above range, there are not sufficiently exhibited an effect of protecting the hair to prevent the hair from suffering damage and an effect of imparting luster and moisture to the hair. Even if the silylated peptide is used in a concentration exceeding the above range, no further increase in the effects is obtained and the hair rather becomes sticky by excess adsorption of the silylated peptide.

The hairdye composition according to the present invention can be prepared in a conventional manner according to known recipes excepting the use of the silylated peptide (I). Therefore, with respect to the components other than the silylated peptide (I), any of those usable for hairdyes can be used in the present invention. Also, the hairdye composition of the present invention can be prepared as a permanent hairdye or as a temporary hairdye. In the preparation of the hairdye composition, the silylated peptide may be added to an already prepared hairdye or may be mixed with other components to prepare a hairdye composition.

For example, in case of incorporating the silylated peptide (I) into a permanent hairdye composition of two package type, the silylated peptide may be incorporated into any of the first composition and the second composition, but is usually added to the first composition.

In case of a two-package oxidation type hairdye composition, in general the first composition contains an oxidation dye (dye precursor) and optionally a coupler, and the second composition contains an oxidizing agent.

Any of oxidation dyes as conventionally used in the first composition can be used in the present invention. Examples of the oxidation dye are, for instance, a phenylenediamine compound such as p-phenylenediamine or N-phenyl-p-phenylenediamine, a tolueneamine compound such as a toluene-2,5-diamine or toluene-3,4-diamine, an aminophenol compound such as p-aminophenol or p-methylaminophenol, an aminonitrophenol such as o-amino-m-nitrophenol, a diaminopyridine such as 2,6-diaminopyridine, and the like.

Generally used couplers are, for instance, m-phenylenediamine, toluene-2,4-diamine, m-aminophenol, resorcinol, catechol, and the like.

Examples of the oxidizing agent used in the second composition are, for instance, hydrogen peroxide, sodium perborate, sodium peroxide, and the like.

Various other additives as shown below can be used so long as the effects of the present invention are not impaired.

For example, the hairdye first composition may contain a surfactant such as a non-ionic, anionic, cationic or amphoteric surfactant, a dissolving assistant such as glycerol or propylene glycol, a humectant, a viscosity modifier such as carboxymethylcellulose or hydroxyethylcellulose, a pH adjusting agent, a perfume, and other known additives.

Any of conventionally used dyes and pigments can be used in the temporary hairdye composition of the present invention. Examples of such colorants are, for instance, a pigment such as titanium oxide or carbon black, a triphenylmethane dye, an azo dye, a quinoline dye, a xanthane dye, an acridine dye, an azine dye, an oxazine dye, an indigoid dye, an anthraquinone dye, a stilbene dye, a thiazol dye, and the like.

The temporary hairdye composition may contain, as occasion demands, various resins, e.g. an acrylate or methacrylate copolymer such as a copolymer of acrylic acid ester or methacrylic acid ester, and a copolymer of vinylpyrrolidone and vinyl acetate.

The temporary hairdye composition may also contain other additives as mentioned above, such as a viscosity modifier, a surfactant, a pH adjusting agent, a humectant and a perfume.

[Aqueous hair dressing containing silylated peptide]

Since the silylated peptide (I) is soluble in water and is composed of a silyl functional group portion and a peptide portion, the silylated peptide, if incorporated into an aqueous hair dressing composition, is sorbed by a hair through the sorption action of the peptide portion to protect the hair, to restore a damaged hair and to impart moisture to the hair. It also serves, based on the silyl functional group portion sorbed by the hair through the peptide portion, to smooth the hair, to impart luster or gloss to the hair, to improve the combability of the hair and to prevent the hair from splitting owing to combing. Moreover, since the silylated peptide (I) is soluble in water, it is excellent in storage stability in aqueous hair dressing compositions. The aqueous hair dressing compositions according to the present invention is explained below in detail in comparison with an aqueous hair dressing composition containing no silylated peptide.

As a hair dressing, there has been used an oil hair dressing such as pomade or hair oil wherein a stickiness and luster are imparted to the hair by a vegetable oil or mineral oil used as the main component. Recently, an aqueous hair dressing which is less oily, such as hair liquid, set lotion, hair styling gel or hair styling mousse, is popularly used.

These aqueous hair dressings are incorporated with a water-soluble polymer setting agent in order to impart a setting power and a luster to the hair. Also, it has been attempted to incorporate a silicone oil and a hydrolysis product of proteins into these aqueous hair dressings, as practiced in other cosmetics, in pursuit of more natural luster and elasticity of hair. However, silicone oils are generally hydrophobic and have a problem, excepting very slight silicone oils, that they are difficult to incorporate into aqueous hair dressings.

Also, high molecular weight silicone oils are easy to sorb to a no or little damaged hydrophobic hair, but are hard to sorb to a damaged hair, namely a rather hydrophilic hair, so they have a problem that the properties thereof cannot be sufficiently exhibited to damaged hairs. Hydrolysis products of proteins are very useful for restoring a hair which has been damaged to elute protein component in the hair by hair washing or the like. However, these hydrolyzed proteins have problems that because the hydrolyzed proteins are generally water-soluble substances, the amount of use is limited when incorporated into aqueous hair dressings containing oils, fats or alcohols, and the hydrolyzed proteins may coagulate to deposit during the storage.

In contrast, since the silylated peptide (I) is soluble in water and has a silyl functional group portion and a peptide portion, it produces excellent effects as mentioned above on the basis of actions of the silyl functional group portion and the peptide portion.

It is preferable that the content of the silylated peptide (I) in the aqueous hair dressing composition is from 0.1 to 20% by weight, especially from 0.5 to 15% by weight. If the content of the silylated peptide is less than the above range, the effect of protecting hair to prevent it from being damaged, the effect of imparting luster and moisture to hair and the effect of improving the combability are not sufficiently exhibited. Even if the silylated peptide is used in a concentration exceeding the above range, no additional increase in the effects is obtained and the hair rather becomes sticky owing to the peptide portion.

Water-soluble polymer setting agents as conventionally used for aqueous hair dressings can be used in the present invention without any restriction, e.g. nutural setting agents, semi-synthetic setting agents and synthetic setting agents. Examples of the natural and semi-synthetic water-soluble polymer setting agents are, for instance, a cellulose derivative such as ethylcellulose, hydroxyethylcellulose or carboxymethylcellulose sodium salt, hydrolysis products of natural proteins and their quaternary ammonium derivatives, and the like. Examples of the synthetic water-soluble polymer setting agent are, for instance, polyvinylpyrrolidone, vinylpyrrolidone-alkylamino acrylate copolymers, vinylpyrrolidone-vinyl acetate copolymer, carboxyvinyl polymers, polyacrylates, polymethacrylates, copolymers of acrylic acid and/or methacrylic acid with alkyl acrylate and/or alkyl methacrylate, and the like.

It is preferable that the content of the water-soluble polymer setting agent in the aqueous hair dressing composition is from 0.1 to 10% by weight, especially from 0.5 to 5% by weight. If the content of the setting agent is less than the above range, the hair setting action is not sufficiently exhibited. If the content of the setting agent is more than the above range, the hair becomes rigid, and in case of natural setting agent, there is a possibility that the hair becomes sticky or the set retention power is lowered, because of increased hygroscopicity.

The aqueous hair dressing composition of the present invention comprehends, for instance, hair liquid, set lotion, hair styling gel, hair styling mousse, hair styling blowing agent, water grease, and the like. These aqueous hair dressing compositions are prepared by adding the silylated peptide (I) and components generally used in the hair dressings such as a water-soluble polymer setting agent to water simultaneously or in optional order.

The aqueous hair dressing composition of the present invention may contain various components other than the water-soluble polymer setting agent so long as the effects of the invention are not impaired, e.g. various kinds of surfactants, thickener, fats and oils, animal and vegetable extracts, peptides obtained by hydrolysis of proteins derived from animals, vegetables and microorganisms, ester derivatives of these peptides, wetting agent, alcohols, amino acids, and the like.

The present invention is more specifically described and explained by means of the following Examples, in which % showing concentration or content is by weight. It is to be understood that the present invention is not limited to these Examples.

EXAMPLE 1

To 50 g (stoichiometric number of moles obtained by measurement of amino nitrogen: 10.6 millimoles) of a 30% aqueous solution of a hydrolyzed collagen (collagen hydrolyzate, a peptide of the formula II wherein the average value of m is 2, the average value of n is 18 and the sum of m+n is 20) was added dropwise a 20% aqueous solution of sodium hydroxide to adjust to pH 9.5, and the solution was heated to 55° C.

In water was dissolved as a silylated agent 2.6 g (1.0 equivalent based on the amino nitrogen of the hydrolyzed collagen) of a silyl compound of the formula (III) wherein $R^6$ is $CH_3$, $R^7$ is $OCH_3$, $R^8$ is $OCH_3$, a is 3 and X is Cl, namely γ-chloropropylmethyldimethoxysilane, to give a 15% aqueous solution of the silyl compound. The obtained solution was adjusted to pH 3.5 with diluted hydrochloric acid, and stirred at 50° C. for 15 minutes to convert methoxy group to hydroxyl group by hydrolysis.

The thus obtained aqueous solution of the hydrolyzed silyl compound was added dropwise to the hydrolyzed collagen solution with stirring at 55° C. over 30 minutes. After the completion of the addition, the mixture was further stirred at 55° C. for 5 hours to complete the silylation reaction.

After the completion of the reaction, the rate of introduction of a silyl functional group (dihydroxymethylsilylpropyl group) to the amino groups of the hydrolyzed collagen was obtained by measuring the amino nitrogen. It was found that the silyl functional group was introduced to 67% of the amino groups —$NH_2$.

After neutralizing the reaction mixture with a diluted hydrochloric acid, it was desalted by an electrodialyser, adjusted to pH 6.5 and concentrated to give 75 g of a 20% aqueous solution of silylated hydrolyzed collagen.

EXAMPLE 2

A 20% aqueous solution of sodium hydroxide was added dropwise to 50 g (stoichiometric number of moles obtained by measurement of amino nitrogen: 15 millimoles) of a 30% aqueous solution of a hydrolyzed wheat protein (wheat protein hydrolyzate, a peptide of the formula II wherein the average value of m is 1.2, the average value of n is 8.8 and the sum of m+n is 10) to adjust to pH 9.5, and the solution was heated to 55° C.

In water was dissolved as a silylating agent 3.1 g (0.9 equivalent based on the amino nitrogen of the hydrolyzed wheat protein) of a silyl compound of the formula (IV) wherein $R^6$ is Cl, $R^7$ is $CH_3$, $R^8$ is Cl and a is 3 namely γ-glycidoxypropylmethyldichlorosilane, to give a 15% aqueous solution of the silyl compound. The obtained solution was stirred for 15 minutes to convert the chlorine atom to hydroxyl group by hydrolysis.

The thus obtained aqueous solution of the hydrolyzed silyl compound was added dropwise to the wheat protein hydrolyzate solution with stirring at 55° C. over 1 hour, and the mixture was further stirred at 55° C. for 5 hours to complete the silylation reaction.

The reaction mixture was neutralized with diluted hydrochloric acid, desalted by an electrodialyzer and concentrated to give 55 g of a 20% aqueous solution of a silylated hydrolyzed wheat protein. The rate of introduction of the silyl functional group was 62%.

EXAMPLE 3

The procedure of Example 1 was repeated except that 50 g of (stoichiometric number of moles obtained by measurement of amino nitrogen: 42 millimoles) of a 30% aqueous solution of a hydrolyzed keratin (wool hydrolyzate, average number of basic amino acid units m=0.6 average number of units n of amino acids other than the basic amino acids= 4.4 m+n=5) was used instead of the hydrolyzed collagen, and 7.5 g (0.8 equivalent based on the amino nitrogen of the hydrolyzed keratin) of a silyl compound of the formula (IV) wherein $R^6$ is $CH_3$, $R^7$ is $OC_2H_5$, $R^8$ is $OC_2H_5$ and a is 3, namely γ-glycidoxypropylmethyldiethoxysilane, was used as the silylating agent, to give 58 g of a 20% aqueous solution of a silylated hydrolyzed keratin. The ethoxy group of the silylating agent was converted to hydroxyl group during the reaction. The rate of introduction of the silyl functional group was 59%.

EXAMPLE 4

The procedure of Example 1 was repeated except that 50 g (stoichiometric number of moles obtained by measurement of amino nitrogen: 18.4 millimoles) of a 30% aqueous solution of a hydrolyzed soybean protein (soybean protein hydrolyzate, average number of basic amino acid units m=0.5, average number of units n of amino acids other than the basic amino acids=5.5, m+n=6) was used instead of the hydrolyzed collagen, and 3.1 g (1.0 equivalent based on the amino nitrogen of the hydrolyzed soybean protein) of a silyl compound of the formula (III) wherein $R^6$ is $OCH_3$, $R^7$ is $OCH_3$, $R^8$ is $OCH_3$, a is 1 and X is Cl, namely chloromethyltrimethoxysilane, was used as the silylating agent, to give 33 g of a 20% aqueous solution of a silylated hydrolyzed soybean protein. The methoxy group of the silylating agent was converted to hydroxyl group during the reaction. The rate of introduction of the silyl functional group was 59%.

EXAMPLE 5

The procedure of Example 1 was repeated except that 50 g (stoichiometric number of moles obtained by measurement of amino nitrogen: 30 millimoles) of a 30% aqueous solution of a hydrolyzed yeast protein (yeast protein hydrolyzate, average number of basic amino acid units m=1.2, average number of units n of amino acids other than the basic amino acids=6.8, m+n=8) was used instead of the hydrolyzed collagen, and 5.3 g (0.8 equivalent based on the amino nitrogen of the hydrolyzed yeast protein) of a silyl compound of the formula (IV) wherein $R^6$ is $CH_3$, $R^7$ is $OC_2H_5$, $R^8$ is $OC_2H_5$ and a is 3, namely γ-glycidoxypropylmethyldiethoxysilane, was used as the silylating agent, to give 48 g of a 20% aqueous solution of a silylated hydrolyzed yeast protein. The ethoxy group of the silylating agent was converted to hydroxyl group during the reaction. The rate of introduction of the silyl functional group was 57%

EXAMPLE 6

A 20% aqueous solution of sodium hydroxide was added dropwise to 10 g of L-lysine hydrochloride (molecular weight 182.6, 54.7 millimoles) dissolved in 100 ml of water to adjust to pH 9.5and the solution was heated to 55° C.

In water was dissolved as a silylating agent 20 g (1.0 equivalent based on the amino nitrogen of L-lysine hydrochloride) of a silyl compound of the formula (III) wherein $R^6$ is $OCH_3$, $R^7$ is $OCH_3$, $R^8$ is $OCH_3$, a is 3 and X is Cl, namely γ-chloropropyltrimethoxysilane, to give a 15% aqueous solution of the silyl compound. The obtained solution was adjusted to pH 3.5 with diluted hydrochloric acid and stirred at 50° C. for 15 minutes to convert the methoxy group to hydroxyl group by hydrolysis.

The thus obtained aqueous solution of the hydrolyzed silyl compound was added dropwise to L-lysine hydrochloride solution with stirring at 55° C. over 30 minutes, and the mixture was further stirred at 55° C. for 5 hours to complete the silylation reaction.

After the completion of the reaction, the rate of introduction of a silyl functional group (trihydroxysilylpropyl group) to the amino groups of L-lysine was obtained by measuring the amino nitrogen. It was found that the rate of introduction of the silyl functional group was 65% and not only α-amino group but also the amino group in the side chain were reacted.

The reaction mixture was neutralized with diluted hydrochloric acid, desalted by an electrodialyzer, neutralized to pH 6.5 and concentrated to give 155 g of a 15% aqueous solution of silylated L-lysine.

EXAMPLE 7

The procedure of Example 6 was repeated except that 10 g of glycyl-L-alanine (molecular weight 146.1, 68.4 millimoles) was used instead of L-lysine hydrochloride, and 13.5 g (0.9 equivalent based on the amino nitrogen of glycyl-L-alanine) of a silyl compound of the formula (IV) wherein $R_6$ is $CH_3$, $R^7$ is $OCH_3$, $R_8$ is $OCH_3$ and a is 1, namely γ-glycidoxymethyldimethoxymethylsilane, was used as the silylating agent, to give 104 g of a 15% aqueous solution of a silylated glycyl-L-alanine. The methoxy group of the silylating agent was converted to hydroxyl group during the reaction. The rate of introduction of the silyl functional group was 55%.

[Storage stability of silylated peptide]

The aqueous solutions of silylated peptide obtained in Examples 1 to 7 were allowed to stand at room temperature (10° to 25° C.) for 90 days, and the presence of a precipitate was visually observed at a fixed period. The storage stability was estimated according to the following criteria.

Rating

+++: Very much precipitate is observed.

++: Much precipitate is observed.

+: Precipitate or turbidity is slightly observed.

−: No precipitate or turbidity is observed.

The above procedure was repeated except that the solutions were stored in a refrigerator at a temperature of about 5° C. and the observation was conducted after the solutions were taken out of the refrigerator and the temperature reached the room temperature.

The results are shown in Table 1.

TABLE 1

| Ex. No. | Peptide source of silylated peptide | Storage manner | Storage term (day) | | | |
|---|---|---|---|---|---|---|
| | | | 15 | 30 | 60 | 90 |
| Ex. 1 | Hydrolyzed collagen | room temp. | − | − | − | − |
| | | cold storage | − | − | − | − |
| Ex. 2 | Hydrolyzed wheat protein | room temp. | − | − | − | − |
| | | cold storage | − | − | − | − |
| Ex. 3 | Hydrolyzed keratin | room temp. | − | − | − | − |
| | | cold storage | − | − | − | − |
| Ex.4 | Hydrolyzed soybean protein | room temp. | − | − | − | − |
| | | cold storage | − | − | − | − |
| Ex. 5 | Hydrolyzed yeast protein | room temp. | − | − | − | − |
| | | cold storage | − | − | − | − |
| Ex. 6 | L-lysine hydrochloride | room temp. | − | − | − | − |
| | | cold storage | − | − | − | − |
| Ex. 7 | Glycyl-L-alanine | room temp. | − | − | − | − |
| | | cold storage | − | − | − | − |

As shown in Table 1, the silylated peptides prepared in Examples 1 to 7 did not cause any turbidity or precipitation in both the storage at room temperature and the storage in refrigerator at 5° C.

[pH stability of silylated peptide]

With respect to the silylated peptides prepared in Examples 1 to 7, 10% aqueous solutions of each of the silylated peptides were adjusted to pH 3, 4, 5, 7, 9 and 10 with 6N hydrochloric acid or 20% sodium hydroxide solution, and allowed to stand at room temperature for 24 hours. The presence of precipitate or turbidity was visually observed, and the pH stability was estimated according to the same estimation criteria as in the storage stability.

The results are shown in Table 2.

TABLE 2

| Ex. No. | Peptide source of silylated peptide | pH | | | | | |
|---|---|---|---|---|---|---|---|
| | | 3 | 4 | 5 | 7 | 9 | 10 |
| Ex. 1 | Hydrolyzed collagen | − | − | − | − | − | − |
| Ex. 2 | Hydrolyzed wheat protein | − | − | − | − | − | − |
| Ex. 3 | Hydrolyzed keratin | + | − | − | − | − | − |
| Ex. 4 | Hydrolyzed soybean protein | − | − | − | − | − | − |
| Ex. 5 | Hydrolyzed yeast protein | + | − | − | − | − | − |
| Ex. 6 | Lysine hydrochloride | + | − | − | − | − | − |
| Ex. 7 | Glycyl-L-alanine | − | − | − | − | − | − |

As shown in Table 2, the silylated keratin hydrolyzed of Example 3, the silylated yeast protein hydrolyzate of Example 5 and the silylated L-lysine of Example 6 showed a slight turbidity at pH 3, but other silylated peptides did not cause any precipitation or turbidity and were stable within the tested full pH range. The silylated peptides of Examples 3, 4 and 6 also did not cause precipitation or turbidity in a pH range over 4. It is considered that since the keratin hydrolyzate and yeast protein hydrolyzate contain many amino acids having amino group at the side chain end, many silyl functional groups are bonded to the peptide portion, so they are apt to reveal a hydrophobic property and, therefore, they caused turbidity at a low pH. It is also considered that in the silylated L-lysine, since two silyl functional groups are bonded to a molecule of L-lysine, turbidity occurred at a low pH.

[Test for Confirming Increase in Tensile Strength of Hair by Silylated Peptide]

Confirmation of increase in tensile strength of a hair by silylated peptide was conducted according to a method described in Journal of SCCJ, Vol. 21, No. 2, 127(1987), "Method for estimating the degree of demage of hairs (I)".

In order to make variation in strength of hairs used in test as small as possible, a hair once bleached so as to make the strength approximately constant was used in the test. The bleaching was conducted by immersing a bundle of 1 g of hairs having a length of 10 cm in 10 g of a mixture of 10% hydrogen peroxide and 10% aqueous ammonia in a ratio of 1:1 by volume for 30 minutes, rinsing with deionized water and drying.

The thus bleached bundle of hairs was treated with a silylated peptide by immersing the bundle in a 5% aqueous solution of the silylated collagen hydrolyzate of Example 1 or the silylated keratin hydrolyzate of Example 3 at 40° C. for 5 minutes, thoroughly rinsing the bundle with deionized water and drying it by a hair dryer. This procedure was repeated 3 times in total, and 30 hairs were taken from the thus treated hair bundle and subjected to the tensile test.

In the tensile test, the major axis and minor axis of the center (5 cm from the ends) of each hair were measured by a micrometer, the cross-sectional area was calculated, the tensile strength of the hair at its center was measured, and the tensile strength per unit cross sectional area was calculated.

For comparison, the above procedure was repeated except that the bleached bundle of hairs was treated with the non-silylated collagen hydrolyzate (m+n=20) or the non-silylated keratin hydrolyzate (m+n=5). The tensile strength of the thus treated hairs was measured together with the non-treated bleached hair.

The results are shown in Table 3.

TABLE 3

| | Tensile strength (kgf/mm$^2$) | Increase in strength to non-treated hair (%) |
|---|---|---|
| Non-treated hair | 28.2 | — |
| Silylated hydrolyzed collagen of Example 1 | 30.9 | 9.57 |
| Hydrolyzed collagen | 30.4 | 7.80 |
| Silyated hydrolyzed keratin of Example 3 | 32.8 | 16.31 |
| Hydrolyzed keratin | 32.1 | 13.83 |

It is observed in Table 3 that the tensile strength of the hair treated with the silylated collagen hydrolyzate of Example 1 increases by about 9.5% based on the non-treated hair, and the tensile strength of the hair treated with the silylated keratin hydrolyzate of Example 3 increases by about 16% based on the non-treated hair. In comparison of these treated hairs with the hair treated with the same hydrolyzed collagen or keratin but not silylated, too, increase in tensile strength is observed. From these results, it would be apparent that the silylated peptide according to the present invention is well sorbed by the hair and contributes to restoration of the strength of damaged hairs.

[Application of Silylated Peptide to Various Cosmetics]

The use of the cosmetic base material comprising the silylated peptide in various cosmetics will be explained below by means of the following Application Examples, wherein all % and parts are by weight unless otherwise noted.

APPLICATION EXAMPLE 1

Three kinds of latex type hair treatment compositions (Product 1 and Comparative Products 1 and 2) were prepared according to the recipes shown in Table 4.

Product 1 contains the silylated wheat protein hydrolyzate of Example 2 as the silylated peptide and stearyldimethyl-benzylammnonium chloride as a cationic surfactant. In Comparative Product 1dimethylpolysiloxane (trade mark "SH200C-500cs", product of Toray Dow Corning Silicone Kabushiki Kaisha) was used as a silicone oil instead of the silylated peptide. In Comparative Product 2, neither of the silylated peptide nor the silicone oil was used.

TABLE 4

| Ingredients (part) | Product 1 | Comparative Product 1 | Comparative Product 2 |
|---|---|---|---|
| Silylated hydrolyzed wheat protein of Ex. 2 (20%) | 10.0 | 0 | 0 |
| Dimethylpolysiloxane | 0 | 2.0 | 0 |
| Stearyldimethylbenzylammonium chloride | 1.5 | 1.5 | 1.5 |

TABLE 4-continued

| Ingredients (part) | Product 1 | Comparative Product 1 | Comparative Product 2 |
|---|---|---|---|
| Polyoxyethylene cetyl ether | 1.0 | 1.0 | 1.0 |
| Behenyl alcohol | 0.5 | 0.5 | 0.5 |
| Cetyl alcohol | 2.0 | 2.0 | 2.0 |
| Olive Oil | 1.5 | 1.5 | 1.5 |
| Ethylene glycol distearate | 0.5 | 0.5 | 0.5 |
| Diglycerol monoisostearate | 1.5 | 1.5 | 1.5 |
| Propylene glycol | 3.0 | 3.0 | 3.0 |
| Mixture of p-hydroxybenzoates and phenoxyethanol (SEISEPT G made by Seiwa Kasei Co., Ltd.) | 0.3 | 0.3 | 0.3 |
| Perfume | proper amount | proper amount | proper amount |
| Sterilized ion-exchange water | balance | balance | balance |
| Total | 100 | 100 | 100 |

Prior to treating hairs with the hair treatment compositions, a bundle of 1 g of hairs having a length of 15 cm was washed with a commercially available shampoo, and 2 g of each of the hair treatment compositions was applied to the washed hair bundle followed by rinsing with hot water. This shampooing and treating procedure was repeated 5 times in total, and the thus treated hairs were then estimated by five women with respect to the manageability, gloss, moisture and combability according to the following 5 ratings.

The results are shown in Table 5 wherein the values shown are the average value from 5 women's estimations.

Rating

5: Very good

4: Good

3: Moderate

2: Bad

1: Very bad

TABLE 5

|  | Product 1 | Comparative Product 1 | Comparative Product 2 |
|---|---|---|---|
| Manageability | 4.6 | 2.4 | 1.6 |
| Gloss | 4.0 | 2.8 | 1.2 |
| Moisture | 5.0 | 2.0 | 1.4 |
| Combability | 4.6 | 3.0 | 1.2 |

As shown in Table 5, the hair treatment composition containing the silylated wheat protein hydrolyzate of Example 2 is superior in all the manageability, gloss, moisture and combability of hairs to the hair treatment composition of Com. Product 1 containing a silicone oil and the hair treatment composition of Com. Product 2 containing neither the silylated peptide nor the silicone oil.

APPLICATION EXAMPLE 2

A treatment rinse (Product 2) was prepared using the silylated keratin hydrolyzate of Example 3 according to the following recipe.

| Ingredients | Amount (part) |
|---|---|
| Silylated hydrolyzed keratin of Ex. 3 (20%) | 20.0 |
| Cetanol | 4.0 |
| Stearyltrimethylammonium chloride (29%) | 2.0 |
| Distearyldimethylammonium chloride (73%) | 1.0 |
| Ethylene glycol stearate (AYACOL EGS-D made by Seiwa Kasei Co., Ltd.) | 3.0 |
| Stearic acid diethylaminoethylamide (AYACOL AMINEAMIDE 50E made by Seiwa Kasei Co., ltd.) | 3.0 |
| Diglycerol isostearate (AYACOL DGMIS made by Seiwa Kasei Co., Ltd.) | 1.5 |
| Propylene glycol | 3.0 |
| Mixture of p-hydroxybenzoates and phenoxyethanol (SEISEPT G made by Seiwa Kasei Co., Ltd.) | 0.5 |
| Perfume | proper amount |
| Sterilized ion-exchange water | balance |
| Malic acid | for adjustment to pH 6.0 |
| Total | 100 |

A treatment rinse as a control was prepared in the same manner as above except that the silylated hydrolyzed keratin was not used and the sterilized ion-exchange water was increased by that portion.

The treatment rinse of Product 2 and the control treatment rinse were applied to hairs. Product 2 showed good moisture-imparting property, combability and brushing ability, thus was superior to the control product in hair conditioning.

APPLICATION EXAMPLE 3

Three kinds of shampoos (Product 3 and Comparative Products 3 and 4) were prepared according to the recipes shown in Table 6.

Product 3 contains the silylated wheat protein hydrolyzate of Example 2 as the silylated peptide. In Comparative Product 3, octamethyltrisiloxane (trade mark "SH200C-1cs", product of Toray Silicone Kabushiki Kaisha) was used as a silicone oil instead of the silylated peptide. In Comparative Product 4, neither of the silylated peptide nor the silicone oil was used.

Also, in these shampoos, non-ionic surfactant polyoxyethylene(10) nonylphenyl ether was used alone as the surfactant.

TABLE 6

| Ingredients (part) | Product 3 | Comparative Product 3 | Comparative Product 4 |
| --- | --- | --- | --- |
| Silylated hydrolyzed wheat protein of Ex. 2 (20%) | 10.0 | 0 | 0 |
| Octamethyltrisiloxane (SH200C-1cs made by Toray Silicone K.K.) | 0 | 2.0 | 0 |
| Polyoxyethylene (10) nonylphenyl ether | 16.1 | 16.1 | 16.1 |
| Lauric acid diethanolamide | 8.0 | 8.0 | 8.0 |
| Lauryldimethylamine oxide | 2.5 | 2.5 | 2.5 |
| Mixture of p-hydroxybenzoates and phenoxyethanol (SEISEPT G made by Seiwa Kasei Co., Ltd.) | 0.5 | 0.5 | 0.5 |
| Perfume | proper amount | proper amount | proper amount |
| Sterilized ion-exchange water | balance | balance | balance |
| Total | 100 | 100 | 100 |

A bundle of 1 g of hairs having a length of 10 cm was washed with 0.5 g of each of the thus prepared shampoos and hot water, rinsed with hot water and dried by a hair dryer. This procedure was repeated 5 times in total. The thus shampooed hairs were estimated by five women with respect to gloss, smoothness, combability with feeling of touch of foams in shampooing such as softness and smoothness according to the 5 ratings shown in Application Example 1.

The results are shown in Table 7 wherein the values are average values.

TABLE 7

|  | Product 3 | Comparative Product 3 | Comparative Product 4 |
| --- | --- | --- | --- |
| Hair after shampooing |  |  |  |
| Gloss | 4.6 | 3.2 | 2.0 |
| Smoothness | 4.4 | 3.0 | 2.0 |
| Combability | 4.8 | 3.4 | 1.8 |
| Foams in shampooing |  |  |  |
| Softness | 4.8 | 3.0 | 2.0 |
| Smoothness | 4.4 | 3.8 | 2.4 |

As shown in Table 7, the shampoo of Product 3 containing the silylated wheat protein hydrolyzate of Example 2 is superior in every estimation items to the comparative shampoo of Com. Product 3 containing a silicone oil (octamethyltrisiloxane) and the comparative shampoo of Com. Product 4 containing neither the silylated peptide nor the silicone oil. These results clearly show that excellent effects are obtained by incorporation of the silylated peptide according to the present invention into shampoos.

APPLICATION EXAMPLE 4

Two kinds of shampoos (Product 4 and Comparative Product 5) were prepared according to the recipes shown in Table 8.

Product 4 contains the silylated keratin hydrolyzate of Example 3 as the silylated peptide, and Comparative Product 5 contains octamethyltrisiloxane (trade mark "SH200C-1cs", product of Toray Dow Corning Silicone Kabushiki Kaisha) as a silicone oil instead of the silylated peptide.

In these shampoos, an anionic surfactant, potassium cocoyl hydrolyzed collagen (potassium salt of an acylation product of a protein-derived peptide with coconut oil fatty acid), was used as the main component of the surfactant to which a minor amount of a cationic surfactant, stearyltimethylammonium chloride, was added.

TABLE 8

| Ingredients (part) | Product 4 | Comparative Product 5 |
| --- | --- | --- |
| Silylated keratin hydrolyzate of Ex. 3 (20%) | 2.5 | 0 |
| Octamethyltrisiloxane | 0 | 0.5 |
| Potassium cocoyl hydrolyzed collagen (35%) (PROMOIS ECP made by Seiwa Kasei Co., Ltd.) | 50.0 | 50.0 |
| Coconut fatty acid diethanolamide | 3.5 | 3.5 |
| Stearyltrimethylammonium chloride (30%) | 3.3 | 3.3 |
| Mixture of p-hydroxybenzoates and phenoxyethanol (SEISEPT G made by Seiwa Kasei Co., Ltd.) | 0.5 | 0.5 |
| Perfume | proper amount | proper amount |
| Sterilized ion-exchange water | balance | balance |
| Total | 100 | 100 |

The above two kinds of shampoos were estimated by 10 persons (7 women and 3 men) as to which is better with respect to foaming, smoothness of foams and finger combability of a hair during shampooing, creaky feeling and finger combability of the hair during rinsing with hot water, and manageability, gloss, smoothness and combability of the hair rinsed and dried.

The results are shown in Table 9.

TABLE 9

|  | Number of persons who answered "Product 4 is better" | Number of persons who answered "Com. Product 5 is better" | Number of persons who answered "cannot tell difference" |
| --- | --- | --- | --- |
| In shampooing |  |  |  |
| Foaming | 8 | 0 | 2 |
| Smoothness of foam | 9 | 0 | 1 |
| Finger combability of hair | 9 | 1 | 0 |
| Hair in rinsing |  |  |  |
| Creaky feeling | 7 | 1 | 2 |
| Finger combability | 8 | 1 | 1 |
| Hair after |  |  |  |

TABLE 9-continued

| | Number of persons who answered "Product 4 is better" | Number of persons who answered "Com. Product 5 is better" | Number of persons who answered "cannot tell difference" |
|---|---|---|---|
| shampooing | | | |
| Manageability | 8 | 0 | 2 |
| Gloss | 8 | 0 | 2 |
| Smoothness | 9 | 0 | 1 |
| Combability | 10 | 0 | 0 |

From the results shown in Table 9, it would be apparent that the Product 4 shampoo containing a silylated peptide is superior in all tested items to the Comparative Product 5 shampoo containing a silicone oil (octamethyltrisiloxane). The reason is considered that the silylated keratin hydrolyzate is well sorbed to the hair through the keratin hydrolyzate portion (peptide portion) whereby the silyl functional group bonded to the keratin hydrolyzate sufficiently exhibit its effects, whereas the silicone oil is difficult to be sorbed to the hair.

APPLICATION EXAMPLE 5

Two kinds of permanent waving lotions to be used in the first stage of the waving treatment (Product 5 and Comparative Product 6) were prepared according to the recipes shown in Table 10.

TABLE 10

| Ingredients (part) | Product 5 | Comparative Product 6 |
|---|---|---|
| Silylated soybean protein hydrolyzate of Ex. 4 (20%) | 25.0 | 0 |
| Ammonium thioglycolate | 12.0 | 12.0 |
| Monoethanolamine | 1.8 | 1.8 |
| Polyoxyethylene (15) lauryl ether | 0.5 | 0.5 |
| Edetate disodium | 0.1 | 0.1 |
| Aqueous ammonia (25%) | 1.6 | 1.6 |
| Perfume | proper amount | proper amount |
| Sterilized ion-exchange water | balance | balance |
| Total | 100 | 100 |

A bundle of 1 g of hairs having a length of 15 cm was wound on a rod having a diameter of 1 cm, and thereto was applied each of the waving lotions. After allowing to stand for a time and washing with water, a 6% aqueous solution of sodium bromate was applied to the hair bundle and allowed to stand for a time. The hair bundle was unfastened from the rod, washed with water and dried.

Such a waving treatment was conducted one time, 3 times or 6 times, and the appearance and feeling of touch of the waved hairs were estimated by five women in 5 ratings (5: very good, 4: good, 3: moderate, 2: bad, 1: very bad).

The results are shown in Table 11, wherein the values shown are average values.

TABLE 11

| | Product 5 | Comparative Product 6 |
|---|---|---|
| Appearance of hair after treatment (gloss, moisture) | | |
| treating once | 4.2 | 3.0 |
| treating three times | 4.0 | 2.6 |
| treating six times | 4.0 | 2.2 |
| Feel of hair after treatment (touch, finger combability) | | |
| treating once | 4.2 | 2.4 |
| treating three times | 4.2 | 2.0 |
| treating six times | 4.0 | 1.8 |

As shown in Table 11, the permanent waving lotion of Product 5 containing the silylated soybean protein hydrolyzate of Example 4 is superior in appearance and feel of the waved hair to the permanent waving lotion of Comparative Product 6 containing no silylated peptide. These results clearly show that excellent effects are obtained by incorporation of the silylated peptide according to the present invention into permanent waving lotions.

APPLICATION EXAMPLE 6

Three kinds of permanent waving lotions (Product 6 and Comparative Products 7 and 8) were prepared according to the recipes shown in Table 12.

Product 6 contains the silylated collagen hydrolyzate of Example 1 as the silylated peptide and benzalkonium chloride as a cationic surfactant. In Comparative Product 7, methylphenylpolysiloxane (trade mark "SH556", product of Toray Dow Corning Silicone Kabushiki Kaisha) was used as a silicone oil instead of the silylated peptide. In Comparative Product 8, neither of the silylated peptide nor the silicone oil was used. In case of Comparative Product 7, the waving lotion was used after thoroughly stirring because of separation of the silicone oil.

TABLE 12

| Ingredients (part) | Product 6 | Comparative Product 7 | Comparative Product 8 |
|---|---|---|---|
| Silylated collagen hydrolyzate of Ex. 1 (20%) | 20.0 | 0 | 0 |
| Methylphenylpolysiloxane | 0 | 4.0 | 0 |
| Benzalkonium chloride (50%) | 1.0 | 1.0 | 1.0 |
| Ammonium thioglycolate (50%) | 12.0 | 12.0 | 12.0 |
| Monoethanolamine | 0.7 | 0.7 | 0.7 |
| Aqueous ammonia (28%) | 0.7 | 0.7 | 0.7 |
| Ammonium bicarbonate | 3.5 | 3.5 | 3.5 |
| Edetate disodium | 0.1 | 0.1 | 0.1 |
| Carboxymethylcellulose sodium salt | 0.2 | 0.2 | 0.2 |
| Sterilized ion-exchange water | balance | balance | balance |
| Total | 100 | 100 | 100 |

A bundle of 1 g of hairs having a length of 15 cm was wound on a rod having a diameter of 1 cm, and thereto was applied each of the waving lotions. After allowing to stand for a time and washing with water, a 6% aqueous solution of sodium bromate was applied to the hair bundle and allowed to stand for a time. The hair bundle was unfastened from the rod, washed with water and dried.

The flexibility, gloss and moisture of the waved hairs were estimated by 10 persons (7 women and 3 men) in 3 ratings (2: the best waved hair of three, 1: waved hair ranked next, 0: poor).

The results are shown in Table 13 wherein the values shown are the average values from ten persons' estimations.

With respect to the hairs after the permanent waving treatment, the tensile strength of the hairs and the amount of cysteic acid in the hairs were measured.

In the tensile test, 30 hairs were taken from each of the treated hair bundles, and the tensile strength thereof was measured as follows: The major axis and minor axis of a hair at the position to be tested (namely the center of 15 cm hair) were measured by a micrometer, and the cross sectional area was calculated. Pressure sensitive adhesive tapes (Scotti Filament Tape made by Sumitomo S3M Limited) were adhered to the hair at the positions each spaced at 0.5 mm from the center in front of and behind the center. The tape-adhering portions were fixed to clamps of a tensile tester (rheometer made by Fudo Kogyo Kabushiki Kaisha). The tensile strength at break of the hair was measured, and the tensile strength per unit cross section (kgf/mm$^2$) was calculated based on the cross sectional area measured previously.

The cysteic acid content in a hair was determined by adding 2 g of 6N hydrochloric acid to 0.1 g of a hair, completely hydrolyzing the hair at 105° C. for 20 hours and measuring the cysteic acid content (μmole/g) by an automatic amino acid analyser. The cysteic acid content in hair shows a degree of damage of a hair, and the smaller the value, the less the damage of the hair.

The results of the measurment are shown in Table 13.

TABLE 13

|  | Product 6 | Comparative Product 7 | Comparative Product 8 |
| --- | --- | --- | --- |
| Hair after treatment |  |  |  |
| Flexibility | 1.8 | 0.6 | 0.6 |
| Gloss | 2.0 | 1.0 | 0.0 |
| Moisture | 2.0 | 0.8 | 0.2 |
| Tensile strength of hair (kgf/mm$^2$) | 32.2 | 28.3 | 27.9 |
| Cysteic acid content in hair (μmol/g) | 72 | 85 | 78 |

It is observed in Table 13 that the permanent waving lotion of Product 6 containing the silylated collagen hydrolyzate is superior to the permanent waving lotions of Com. Products 7 and 8 in flexibility, gloss and moisture and has a larger tensile strength and a less cysteic acid content. These results clearly show that the silylated collagen hydrolyzate according to the present invention is well sorbed to hairs, thus it prevents the hair from being damaged by permanent waving treatment and increases the tensile strength of the hair.

APPLICATION EXAMPLE 7

Three kinds of hair dyes (first lotion) (Product 7 and Comparative Products 9 and 10) were prepared according to the recipes shown in Table 14.

TABLE 14

| Ingredients (part) | Product 7 | Comparative Product 9 | Comparative Product 10 |
| --- | --- | --- | --- |
| Silylated yeast protein hydrolyzate of Ex. 5 (20%) | 12.5 | 0 | 0 |

TABLE 14-continued

| Ingredients (part) | Product 7 | Comparative Product 9 | Comparative Product 10 |
| --- | --- | --- | --- |
| Dimethylpolysiloxane | 0 | 2.5 | 0 |
| p-Phenylenediamine | 2.0 | 2.0 | 2.0 |
| Resorcinol | 1.6 | 1.6 | 1.6 |
| Isopropanol | 10.0 | 10.0 | 10.0 |
| Propylene glycol | 12.0 | 12.0 | 12.0 |
| Oleic acid | 20.0 | 20.0 | 20.0 |
| Bis-2-hydroxyethyl-sorbitanamine | 9.0 | 9.0 | 9.0 |
| Hydroxyethyl-stearylamide | 6.0 | 6.0 | 6.0 |
| Aqueous ammonia (28%) | 10.0 | 10.0 | 10.0 |
| Sodium sulfite | 0.5 | 0.5 | 0.5 |
| Edetate disodium | 0.5 | 0.5 | 0.5 |
| Sterilized ion-exchange water | balance | balance | balance |
| Total | 100 | 100 | 100 |

A second lotion was prepared according to the following recipe.

| Ingredients of second lotion | Part |
| --- | --- |
| Stearic acid | 1.0 |
| Glycerol monostearate | 1.5 |
| Polyoxyethylene (20) oleyl ether | 1.0 |
| Hydrogen peroxide (35%) | 15.5 |
| Sterilized deionized water | balance to 100 |

Equal amounts of the hair dye first lotion (Product 7 or Comparative Product 9 or 10) and the second lotion were mixed, and the resulting mixture was applied to a bundle of 1 g of hairs having a length of 15 cm. The hair bundle was then allowed to stand for 30 minutes, rinsed with hot water, washed with a 2% aqueous solution of polyoxyethylene nonylphenyl ether, and dried by a hair drier.

The uniform dyability, gloss, moisture and combability of the thus dyed hairs were estimated by ten persons (6 women and 4 men) in 5 ratings (5: very good, 4: good, 3: moderate, 2: bad, 1: very bad).

The tensile strength of the dyed hairs was also measured in the same manner as in Application Example 6.

The results are shown in Table 15.

TABLE 15

|  | Product 7 | Comparative Product 9 | Comparative Product 10 |
| --- | --- | --- | --- |
| Hair after treatment |  |  |  |
| Uniform dyability | 4.4 | 2.8 | 3.0 |
| Gloss | 4.6 | 3.4 | 2.0 |
| Moisture | 4.4 | 3.0 | 2.0 |
| Combability | 4.6 | 3.6 | 1.6 |
| Tensile strength (kgf/mm$^2$) | 30.4 | 28.2 | 27.8 |

It is observed in Table 15 that the hair dye of Product 7 containing the silylated yeast protein hydrolyzate of Example 5 is superior in all test items, i.e. uniform dyability, gloss, moisture and combability to the hair dye of Comparative Product 9 containing a silicone oil (dimethylpolysiloxane) and the hair dye of Comparative Product 10 containing neither silylated peptide nor silicone oil.

Also, with respect to the tensile strength, it is observed that the hair dyed with the hair dye of Product 7 has a higher tensile strength by about 5% than the hair dyed with the hair dye of Comparative Product 10 containing neither silylated peptide nor silicone oil. From such a result, it would be apparent that the silylated yeast protein hydrolyzate protects hairs from suffering damage from a chemical treatment in hair dyeing.

APPLICATION EXAMPLE 8

Three kinds of shampoo type hair dyes (first lotion) (Product 8 and Comparative Products 11 and 12) were prepared according to the recipes shown in Table 16.

TABLE 16

| Ingredients (part) | Product 8 | Comparative Product 11 | Comparative Product 12 |
|---|---|---|---|
| Silylated keratin hydrolyzate of Ex. 3 (20%) | 20.0 | 0 | 0 |
| Octamethyltrisiloxane | 0 | 4.0 | 0 |
| p-Aminophenol | 0.2 | 0.2 | 0.2 |
| o-Aminophenol | 0.3 | 0.3 | 0.3 |
| Nitro-p-phenylenediamine | 0.5 | 0.5 | 0.5 |
| Sodium lauryl sulfate (35%) | 30.0 | 30.0 | 30.0 |
| Coconut fatty acid diethanolamide | 5.0 | 5.0 | 5.0 |
| Polyoxyethylene nonyl-phenyl ether | 3.0 | 3.0 | 3.0 |
| Glycerol | 2.0 | 2.0 | 2.0 |
| Edetate disodium | 0.3 | 0.3 | 0.3 |
| Sodium cocoyl hydrolyzed collagen (30%) | 5.0 | 5.0 | 5.0 |
| Citric acid | 0.1 | 0.1 | 0.1 |
| Purified water | balance | balance | balance |
| Total | 100 | 100 | 100 |

A second lotion was prepared according to the following recipe.

| Ingredients of second lotion | Part |
|---|---|
| Hydrogen peroxide (35%) | 8.0 |
| Cetanol | 0.3 |
| Polyoxyethylene cetyl ether | 0.2 |
| Purified water | balance to 100 |

Equal amounts of the hair dye first lotion (Product 8 or Comparative Product 11 or 12) and the second lotion were mixed, and about 2 g of the resulting mixture was applied to a bundle of 1 g of hairs having a length of 10 cm. The hair bundle was then allowed to stand for 2 minutes, rinsed with tepid water, and dyed again in the same manner as above. After repeating the dyeing procedure 5 times in total, the dyed hair bundle was washed with a 2% aqueous solution of polyoxyethylene nonylphenyl ether, rinsed with tepid water and dried by a hair drier.

The gloss, moisture and combability of the thus dyed hairs were estimated by ten persons in 5 ratings (5: very good, 4: good, 3: moderate, 2: bad, 1: very bad).

Further, the dyed hairs were washed 5 times with a 2% aqueous solution of polyoxyethylene nonylphenyl ether, and the shade of color, moisture, gloss and combability of the thus shampooed hairs were estimated in the same manner. The estimation of the shade of color was conducted in five reatings wherein the shade of color of a hair just after dyeing is set as point 5 and the shade of color of a non-dyed hair is set as point 1. The higher the value of the color shade of the shampooed hair, the less the discoloration owing to shampooing.

Also, the tensile strength and cysteic acid content of the hairs after dyeing were measured.

The results are shown in Table 17 wherein the values shown are the average values.

TABLE 17

|  | Product 8 | Comparative Product 11 | Comparative Product 12 |
|---|---|---|---|
| Hair after dyeing |  |  |  |
| Moisture | 4.8 | 2.2 | 1.6 |
| Gloss | 4.8 | 3.2 | 1.6 |
| Combability | 4.4 | 3.0 | 1.4 |
| Hair after shampooing 5 times |  |  |  |
| Moisture | 4.2 | 1.8 | 1.4 |
| Gloss | 4.2 | 2.2 | 1.4 |
| Combability | 4.0 | 2.4 | 1.4 |
| Shade of color | 4.0 | 2.8 | 3.0 |
| Tensile strength of hair (kgf/mm$^2$) | 31.9 | 30.0 | 28.3 |
| Cysteic acid content in hair (μmol/g) | 254 | 319 | 360 |

It is observed in Table 17 that the hair dye containing the silylated keratin hydrolyzate of Example 3 is superior to the hair dyes of Comparative Products 11 and 12 in test items showing the state of hair such as moisture, gloss and combability. These properties of the dyed hair are not decreased so much even after shampooing 5 times, and the discoloration is also slight. It is also observed that the hair dyed with Product 8 has a larger tensile strength and a less cysteic acid content.

APPLICATION EXAMPLE 9

A bundle of 1 g of hairs having a length of 15 cm was subjected to permanent waving treatment with Comparative Product 6 in the same manner as in Application Example 5.

Three kinds of hair styling blow compositions (Product 9 and Comparative Products 13 and 14) were prepared according to the recipes shown in Table 18. Each of them placed in a pump spraying container was uniformly sprayed onto the wet waved hair bundle unfastened from a rod, and the sprayed hair bundle was dried by a hair dryer.

TABLE 18

| Ingredients (part) | Product 9 | Comparative Product 13 | Comparative Product 14 |
|---|---|---|---|
| Silylated yeast protein hydrolyzate of Ex. 5 (20%) | 10.0 | 0 | 0 |
| Octamethyltrisiloxane | 0 | 10.0 | 0 |
| Glycerol monostearate | 0.5 | 0.5 | 0.5 |
| Polymethyl methacrylate | 3.0 | 3.0 | 3.0 |
| Stearyltrimethylammonium chloride | 1.0 | 1.0 | 1.0 |
| Glycerol | 2.0 | 2.0 | 2.0 |
| Ethanol | 10.0 | 10.0 | 10.0 |
| Sterilized ion-exchange water | balance | balance | balance |
| Total | 100 | 100 | 100 |

The gloss, moisture and combability of the thus treated hairs were estimated by 10 persons (6 women and 4 men) in 5 ratings (5: very good, 4: good, 3: moderate, 2: bad, 1: very bad). Also, 30 hairs were taken from each of the treated hair bundles and subjected to the tensile test.

The results are shown in Table 19 wherein the values shown are the average value.

TABLE 19

|  | Product 9 | Comparative Product 13 | Comparative Product 14 |
|---|---|---|---|
| Hair after permanent waving treatment |  |  |  |
| Gloss | 2.0 | 1.0 | 0.0 |
| Moisture | 2.0 | 1.0 | 0.0 |
| Combability | 2.0 | 1.0 | 0.0 |
| Tensile strength (kgf/mm$^2$) | 31.8 | 29.7 | 30.2 |
| Increase in strength to non-treated hair (%) | 11.97 | 4.58 | 6.34 |

As apparent from the results shown in Table 19, the hair styling blow composition of Product 9 is superior in all of gloss, moisture and combability of hair to the hair styling blow compositions of Comparative Products 13 and 14. It is also observed that the tensile strength of the hair treated with the hair styling blow composition of Product 9 increases by about 12% based on the non-treated hair, and the increase is about 2.6 times the increase in tensile strength of the hair treated with Comparative Product 13 containing a silicone oil (octamethyltrisiloxane) and about 2 times the increase in tensile strength of the hair treated with Comparative Product 14 containing no silicone oil. From these results, it is apparent that the silylated yeast protein hydrolyzate exhibits excellent actions to prevent hairs from suffering damage and to restore damaged hairs by sorption to the hairs.

APPLICATION EXAMPLE 10

A hair liquid (Product 10) was prepared according to the recipe shown below by using the silylated wheat protein hydrolyzate obtained in Example 2.

Another hair liquid (Comparative Product 15) was also prepared in the same manner except that the silylated wheat protein hydrolyzate was not used and the amount of sterilized ion-exchange water was increased by that portion.

| Ingredients | Part |
|---|---|
| Silylated wheat protein hydrolyzate (m + n = 8) (20%) | 12.5 |
| Alkyl acrylate-alkyl methacrylate copolymer (PLASIZE L-53P made by Goou Kagaku K.K.) (50%) | 1.5 |
| Polyoxypropylene(40) butyl ether | 20.0 |
| Ethanol | 50.0 |
| Edetate disodium | 0.1 |
| Perfume | proper amount |
| Sterilized ion-exchange water | balance to 100 |

The thus prepared hair liquids were tested by five men by using once every day the hair liquid of Comparative Example 15 for first 5 days and the hair liquid of Product 10 for the next 5 days, and estimating the manageability, gloss, moisture and combability of them as to whether these properties observed when Product 10 was used, become better or worse or were not different as compared with those observed when Comparative Product 15 was used.

The results are shown in Table 20.

TABLE 20

|  | Number of persons who answered "getting better" | Number of persons who answered "getting worse" | Number of persons who answered "not different" |
|---|---|---|---|
| Hair after treating |  |  |  |
| Manageability | 5 | 0 | 0 |
| Moisture | 5 | 0 | 0 |
| Combability | 5 | 0 | 0 |
| Split hair | 5 | 0 | 0 |

As shown in Table 20 after the use of the hair liquid of Product 10 containing the silylated wheat protein hydrolyzate of Example 2, all panelists answered that the manageability, gloss, moisture and combability were improved as compared with before use. It is apparent that the silylated wheat protein hydrolyzate has actions to impart gloss and moisture to hairs, to improve the combability and to improve the hair setting property.

APPLICATION EXAMPLE 11

A cleansing preparation (Product 11) was prepared according to the following recipe by using the silylated L-lysine obtained in Example 6.

Another cleansing preparation was also prepared in the same manner except that the silylated L-lysine was replaced with sterilized ion-exchange water.

| Ingredients | Part |
|---|---|
| Silylated L-lysine of Ex. 6 (15%) | 6.7 |
| Potassium cocoyl hydrolyzed collagen (PROMOIS ECP-C made by Seiwa Kasei Co., Ltd.) (35%) | 40.0 |
| Sodium coconut fatty acid taurate (30%) | 40.0 |
| Lauric acid diethanolamide | 3.0 |
| Polyethylene glycol monostearate | 4.5 |
| Polyethylene glycol dioleate | 4.0 |
| Mixture of p-hydroxybenzoic acid esters and phenoxyethanol (SEISEPT G made by Seiwa Kasei Co., Ltd.) | 0.5 |
| Perfume | proper amount |
| Sterilized ion-exchange water | balance |
| Malic acid | adjustment to pH 6.0 |
| Total | 100 |

A face was washed with the cleansing preparation of Product 11 containing the silylated L-lysine of Example 6. The gloss, moisture and smoothness of the skin were better than the comparative cleansing preparation containing no silylated L-lysine.

APPLICATION EXAMPLE 12

Three kinds of body shampoos (Product 12 and Comparative Products 16 and 17) were prepared according to the recipes shown in Table 21.

TABLE 21

| Ingredients (part) | Product 12 | Comparative Product 16 | Comparative Product 17 |
|---|---|---|---|
| Silylated glycyl-L-alanine of Ex. 7 (15%) | 13.3 | 0 | 0 |
| Dimethylsiloxane-methyl(polyoxyethylene)siloxane copolymer (SH3746 made by Toray Silicone K.K.) | 0 | 2.0 | 0 |
| Potassium cocoyl hydrolyzed collagen (PROMOIS ECP-C made by Seiwa Kasei Co., Ltd.) (35%) | 28.0 | 28.0 | 28.0 |
| Coconut oil potassium soap (40%) | 7.5 | 7.5 | 7.5 |
| Coconut oil fatty acid diethanolamide | 3.0 | 3.0 | 3.0 |
| Lauric acid diethanolamide | 3.0 | 3.0 | 3.0 |
| Mixture of p-hydroxybenzoates and phenoxyethanol (SEISEPT G made by Seiwa Kasei Co., Ltd.) | 0.5 | 0.5 | 0.5 |
| Sterilized ion-exchange water | balance | balance | balance |
| Total | 100 | 100 | 100 |

Each of the body shampoos was used by ten persons (5 women and 5 men) for a week, provided that three persons used only 4 days (4 times), and was estimated with respect to foam quality (softness and smoothness of foams) in body washing and smoothness and feeling of moistness of the skin after washing in the same three ratings as in Application Example 6.

The results are shown in Table 22 wherein the values shown are the average values from 10 persons' estimations.

TABLE 22

|  | Product 12 | Comparative Product 16 | Comparative Product 17 |
|---|---|---|---|
| Foam quality in shampooing |  |  |  |
| Softness | 1.8 | 1.2 | 0 |
| Smoothness | 1.6 | 1.4 | 0 |
| Skin after shampooing |  |  |  |
| Smoothness | 1.7 | 1.3 | 0 |
| Feeling of moistness | 2.0 | 1.0 | 0 |

From the results shown in Table 21 it is apparent that the body shampoo of Product 12 containing the silylated glycyl-L-alanine of Example 7 makes foams produced in washing soft and smooth and imparts smoothness and feeling of moistness to a skin, and is superior to the body shampoo of Comparative Product 16 containing a silicone oil, dimethylsiloxane-methyl(polyoxyethylene)-siloxane copolymer, and the body shampoo of Comparative Product 17 containing neither silylated peptide nor silicone oil.

As explained above, the base material for cosmetics comprising the silylated peptide according to the present invention imparts gloss and moisture to hairs and improves the combability of hairs if incorporated into hair cosmetics, and makes foams soft and smooth to improve a feel to skin if incorporated into cleansing preparations or shampoos, and imparts gloss and moisture to a skin and smoothes the skin if incorporated into skin cosmetics. The base material for cosmetics comprising the silylated peptide according to the present invention is soluble in water and is excellent in pH stability and storage stability in water, so it does not cause turbidity or precipitation during storage even if incorporated into aqueous hair and skin cosmetics.

In addition to the ingredients used in the Examples, other ingredients can be used in the Examples as set forth in the specification to obtain substantially the same results.

What we claim is:

1. A base material for cosmetics which comprises a silylated peptide of the formula (I):

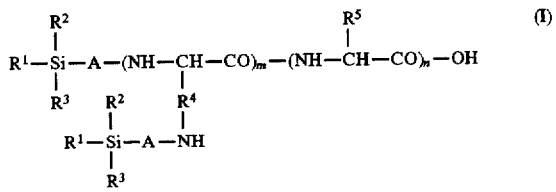

wherein $R^1$, $R^2$ and $R^3$ are the same or different and each is a methyl group or hydroxyl group provided that at least a portion of the total number of $R_1$, $R^2$ and $R^3$ groups consists of hydroxyl groups, $R^4$ is a residue of a basic amino acid having an amino group at the end of a side chain wherein the terminal amino group and the group —CH(NH$_2$)COOH are excluded from said basic amino acid; $R^5$ is a side chain of an amino acid other than said basic amino acid, A is methylene, propylene, —CH$_2$OCH$_2$CH(OH)CH$_2$— or —(CH$_2$)$_3$OCH$_2$CH(OH)CH$_2$— group, m has a value from more than 0 to 100, n has a value from 0 to 100 and m+n has a value from 1 to 100, provided that m and n only show the number of amino acid units, but not the amino acid sequence.

2. A cosmetic composition comprising (A) 0.1 to 30% by weight of a silylated peptide of the formula (I):

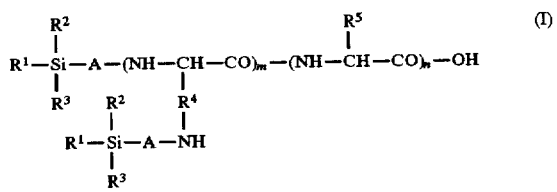

wherein $R^1$, $R^2$ and $R^3$ are the same or different and each is a methyl group or hydroxyl group provided that at least a portion of the total number of $R^1$, $R^2$ and $R^3$ groups consists of hydroxyl groups, $R^4$ is a residue of a basic amino acid having an amino group at the end of a side chain wherein the terminal amino group and the group —CH(NH$_2$)COOH are excluded from said basic amino acid, $R^5$ is a side chain of an amino acid other than said basic amino acid, A is methylene, propylene, —CH$_2$OCH$_2$CH(OH)CH$_2$— or —(CH$_2$)$_3$OCH$_2$CH(OH)CH$_2$— group, m has a value from more than 0 to 100, n has a value from 0 to 100, and m+n has a value from 1 to 100, provided that m and n only show the number of amino acid units, but not amino acid sequence, and (B) a surfactant.

3. A hair treating composition comprising 0.1 to 20% by weight of the silylated peptide of claim 1.

4. The hair treating composition of claim 3, which contains 0.2 to 5% by weight of a cationic surfactant.

5. A shampoo composition comprising 0.1 to 10% by weight of the silylated peptide of claim 1.

6. The shampoo composition of claim 5, which contains 2 to 25% by weight of a surfactant.

7. The shampoo composition of claim 5, which contains 0.1 to 25% by weight of at least one non-cationic surfactant selected from the group consisting of anionic surfactants, non-ionic surfactants and amphoteric surfactants, and 0.2 to 5% by weight of a cationic surfactant.

8. The shampoo composition of claim 7, wherein said non-cationic surfactant is an anionic surfactant selected from the group consisting of amino acid-based surfactants, acylation products of protein-derived peptides and salts of said acylation products.

9. A permanent waving composition suitable for use in the first reduction stage, comprising 0.1 to 15% by weight of the silylated peptide of claim 1.

10. The permanent waving composition of claim 9, which contains 1 to 10% by weight of a reducing agent.

11. The permanent waving composition of claim 9, which contains 0.1 to 5% by weight of a cationic surfactant.

12. A hair dye composition comprising 0.1 to 15% by weight of the silylated peptide of claim 1.

13. An aqueous hair dressing composition comprising 0.1 to 20% by weight of the silylated peptide of claim 1.

14. The hair dressing composition of claim 13, which contains 0.1 to 10% by weight of a water-soluble polymer setting agent.

15. The material of claim 1, wherein m in said formula (I) is from more than 0 to not more than 10.

16. The cosmetic composition of claim 2, wherein m in said formula (I) is from more than 0 to not more than 10.

* * * * *